(12) United States Patent
Meathrel et al.

(10) Patent No.: US 7,927,865 B2
(45) Date of Patent: Apr. 19, 2011

(54) MICROFLUIDIC DEVICES FOR USE IN THE ASSAYING OF BIOLOGICAL FLUIDS

(75) Inventors: William Meathrel, York, PA (US);
Herbert M. Hand, Sr., Bel Air, MD (US); Li-Hung Su, Loganville, PA (US)

(73) Assignee: Adhesives Research, Inc., Glen Rock, PA (US)

( * ) Notice: Subject to any disclaimer, the term of this patent is extended or adjusted under 35 U.S.C. 154(b) by 314 days.

(21) Appl. No.: 12/328,815

(22) Filed: Dec. 5, 2008

(65) Prior Publication Data

US 2009/0081080 A1 Mar. 26, 2009

Related U.S. Application Data

(62) Division of application No. 10/474,920, filed on Oct. 16, 2003, now Pat. No. 7,476,533.

(51) Int. Cl.
*G01N 33/53* (2006.01)

(52) U.S. Cl. ... 435/287.2; 435/287.1; 435/4; 435/287.9; 435/810; 422/56; 422/57; 422/58; 422/61; 436/514; 436/518; 436/169; 436/810

(58) Field of Classification Search .......... 422/56, 422/57, 58, 61; 435/287.1, 4, 287.7, 287.9, 435/810; 436/514, 518, 169, 810
See application file for complete search history.

(56) References Cited

U.S. PATENT DOCUMENTS

| | | |
|---|---|---|
| 3,960,499 A | 6/1976 | White |
| 4,806,312 A | 2/1989 | Greenquist |
| 5,023,052 A | 6/1991 | Nagatomo et al. |
| 5,620,901 A | 4/1997 | Kauvar |
| 5,804,625 A | 9/1998 | Temperante et al. |
| 5,904,824 A | 5/1999 | Oh |
| 5,962,215 A | 10/1999 | Douglas et al. |
| 5,985,675 A | 11/1999 | Charm et al. |
| 6,040,048 A | 3/2000 | Kato et al. |
| 6,087,185 A | 7/2000 | Lee-Own et al. |
| 6,121,508 A | 9/2000 | Bischof et al. |
| 6,150,180 A | 11/2000 | Parce et al. |
| 6,258,548 B1 | 7/2001 | Buck |

(Continued)

FOREIGN PATENT DOCUMENTS

CA 2311496 A1 6/1999

(Continued)

OTHER PUBLICATIONS

Grodzinski et al., Development of Plastic Microfluidic Devices for Sample Preparation, Kluwer Academic Publishers, 3:4, 275-283, 2001, The Netherlands.

(Continued)

*Primary Examiner* — Bao-Thuy L Nguyen
(74) *Attorney, Agent, or Firm* — McNees Wallace & Nurick LLC

(57) ABSTRACT

Diagnostic in-vitro devices for use in the assaying of biological fluids are provided which include cover plates or backing strips which exhibit hydrophilic properties to assist in transport of the biological fluid or retention of same within the device. Exemplary diagnostic devices include lateral flow devices, microfluidic devices and microtiter plates. The devices may also be comprised of low fluorescent material in order to facilitate any diagnostic determination by use of fluorescent emissions. Hydrophilic properties may be imparted to the cover plates or backing strips by physical or chemical treatment thereof. The cover plates or backing strips may exhibit heat sealable or pressure sensitive properties.

15 Claims, 13 Drawing Sheets

U.S. PATENT DOCUMENTS

| | | |
|---|---|---|
| 6,284,194 B1 | 9/2001 | Chu |
| 6,413,782 B1 | 7/2002 | Parce et al. |
| 6,881,378 B1 | 4/2005 | Zimmer et al. |
| 7,153,651 B1 | 12/2006 | Drewes et al. |
| 7,238,255 B2 | 7/2007 | Derand et al. |
| 7,553,393 B2 | 6/2009 | Derand et al. |
| 2002/0106710 A1 | 8/2002 | Tuohy et al. |

FOREIGN PATENT DOCUMENTS

| | | |
|---|---|---|
| DE | 3903126 A1 | 2/1989 |
| DE | 3903126 A1 | 8/1989 |
| EP | 0408378 A2 | 1/1991 |
| FR | 2670292 A1 | 6/1992 |
| GB | 2341924 A | 3/2000 |
| WO | 9839645 | 9/1998 |
| WO | 9927364 | 6/1999 |
| WO | 9958245 | 11/1999 |
| WO | 00/50871 | 8/2000 |
| WO | 97/48779 | 8/2000 |
| WO | 0204570 A3 | 1/2002 |
| WO | 02056751 A2 | 7/2002 |
| WO | 2004066822 A2 | 8/2004 |

OTHER PUBLICATIONS

Lee et al., Design and Fabrication of CD-Like Microfluidic Platforms for Diagnostics: Polymer-Based Microfabrication, Kluwer Academic Publishers, 3:4, 339-351, 2001, The Netherlands.

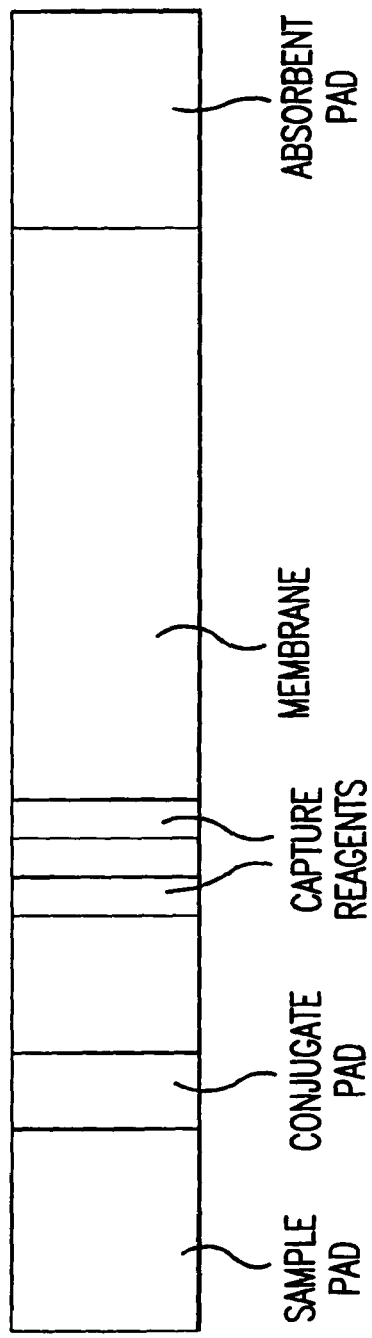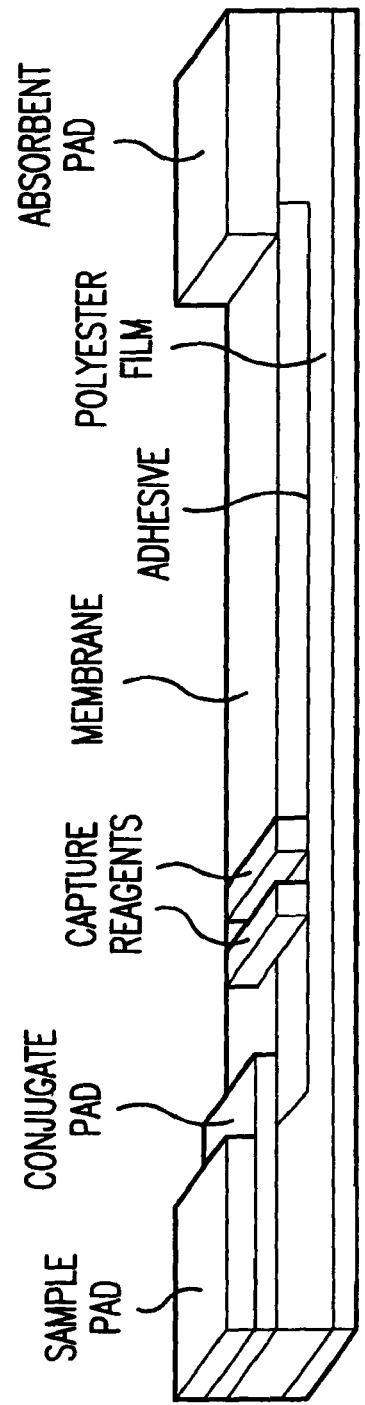

MICROFLUIDIC DEVICES FOR USE IN THE ASSAYING OF BIOLOGICAL FLUIDS

This application is a divisional application under 35 U.S.C. §121 of U.S. patent application Ser. No. 10/474,920, incorporated by reference in its entirety and now U.S. Pat. No. 7,476,533, which entered the national stage under 35 U.S.C. §371 of PCT International Application No. PCT/US02/12329 which has an International filing date of Apr. 19, 2002.

BACKGROUND OF THE INVENTION

This application is directed to novel hydrophilic constructions for in-vitro diagnostic test devices.

Lateral flow test strips are routinely used in medical and other applications to provide convenient and simple analysis of many important chemicals. S. M. Rosen, "Biomarkers of chemical exposure: A new Frontier in Clinical Chemistry", *IVD Technology*, May (1996) p. 22; R. A. Esposito, A. T. Culliford, S. B. Colvin et al., "The Role of the Activated Clotting Time in Herparin Administration and Neutralization for Cardiopulmonary Bypass", *J. Thor. Card. Surg.* 85 (1983), 174-185; C. A. McDonald, P. Syribeys, B. Hazelton, P. Bethea, T. Rigl, S. Hydo, S. J. Kennedy, $93^{rd}$ *General Meeting of American Society Microbiology*, "A rapid 1-step colored particle lateral flow immunoassay for the detection of Group 1 Streptococcal Antigen extracted directly from Throat Swats", 93 (1993), p. 507; and C. Huang and E. Fan, "One Step Immunochromatographic Device and Method of Use", U.S. Pat. No. 5,712,172; A. Pronovost and J. Pawlak, "One Step Urine Creatine Assays", U.S. Pat. No. 5,804,452.

Microtiter plates are used in the handling of liquid material samples during analytical assays for multiple, low volume analysis. Such plates involve the use of an assay plate having multiple depressions or wells, which provide a rapid automated analysis. Typically, such wells have a capacity of 1 microliter. Such microliter plates have a variety of uses, including enzyme assays, receptor-ligand assays, cell based assays, etc. The use of such microliter plates may be either batch-wise, or continuous.

The use of a continuous strip of material having sample wells molded along the length of the strip of material is disclosed in U.S. Pat. No. 4,883,642. This patent discloses means to automatically hold, process, store and analyze biological samples comprised of a ribbon provided with microwells for analysis of multiple samples. The microwells in the ribbon may be protected by an adhered protective film or skin.

Microfluidic devices are also commonly-used in the assaying of biological samples. Such devices comprise a base platform within which are formed a number of capillaries which serve to transport the sample from a receiving portion of the device to a collection portion.

All of the above diagnostic devices are well-known to those skilled in the art.

In-vitro diagnostic devices are used to detect analytes such as nutrients, hormones, therapeutic drugs, drugs-of-abuse and environmental contaminates. In medical diagnostic test devices, biological fluids such as whole blood, plasma, serum, nasal secretions, sputum, saliva, urine, sweat, transdermal exudates, cerebrospinal fluids and the like may be analyzed for specific components that are clinically important for monitoring and diagnosis. In addition, microbiological suspensions and tissues may be homogenized in compatible liquids and the fluid analyzed for specific components. Typically, the specimen fluid is deposited at an inlet port of a suitable in-vitro diagnostic test strip and the sample fluid is drawn into the device by mechanical means such as vacuum or by capillary flow action.

In-vitro diagnostic devices are used in various settings including hospitals, clinics, alternative care sites and in the home. These devices have been developed by various manufacturers to enable clinical professionals and non-professionals to make accurate decisions for the diagnosis and management of medical conditions. Point-of-care devices such are used to analyze blood chemistry such as electrolytes and pH in both clinical and non-clinical locations. Home pregnancy test kits are used to monitor hcG in urine. Diabetics routinely use diagnostic test strips to monitor blood glucose concentrations. Amira Medical, "Glucose Monitor without Fingersticking", *IVD Technology*, July 1999, p. 16.

A number of U.S. and foreign patents describe the use of lateral flow assay devices. U.S. Pat. No. 5,798,27 and corresponding European patent 833159 describe a direct read lateral flow device for detecting small analytes. WO 97/38126 describes a lateral flow device for measuring analytes in whole blood. U.S. Pat. No. 5,804,452 describes a device for the detection of creatinine in biological fluids such as urine in a one step lateral flow sensor. U.S. Pat. No. 5,916,521 describes a vertical flow diagnostic device for the testing of body fluids. WO 99/34191 describes a lateral flow test strip for the detection of an analyte such as beta lactam in milk. See also, U.S. Pat. Nos. 4,857,453; 5,087,556, 5,137,808; 5,712, 170; 5,712,172; 5,804,452; 5,821,073; 5,985,675; 5,989,921; 6,087,175 and 6,103,536.

Various types of capillary flow type diagnostic devices are also known and have been used for some time. Exemplary of such devices are those shown in U.S. Pat. Nos. 6,048,498 and 6,117,395.

OBJECTS AND SUMMARY OF THE INVENTION

It is an object of the present invention to provide diagnostic devices which enable benefits to be achieved not achieved by prior art devices.

It is an object of the present invention to provide lateral flow devices which provide faster and more uniform flow of the sample, uniform wicking of membranes and a uniform capture line.

It is an object of the present invention to provide a microfluidic device which provides uniform wetting and wicking, ease of manufacture, which is non-contaminating to the sample, exhibits controlled evaporation and enables separation of components to be achieved.

It is further an object of the present invention to provide a microtiter plate diagnostic device which exhibits improved wetting, reduces condensation accumulation and serves to enhance the desired diagnostic testing.

In accordance with the above, there is provided a lateral flow in-vitro diagnostic device comprising a housing, means in the housing to introduce a sample to be assayed in the device, means in the housing for fluid collection, and a backing strip having spaced apart first and second ends, the improvement wherein the surface of the backing strip is hydrophilic in character.

In accordance with another embodiment of the invention, there is provided a microfluidic in-vitro diagnostic device comprised of a base having at least one fluid channel within which a fluid sample to be assayed passes from an inlet port to a detection zone, with said at least one fluid channel being sealed by an enclosure surface, the improvement wherein at least one surface of the at least one fluid channel is hydrophilic in character.

In accordance with still another embodiment of the invention, there is provided a microfluidic in-vitro diagnostic device comprised of opposing base portions separated by an adhesive spacer portion having fluid channels therein within which a fluid to be assayed passes from an inlet port to a detection zone, wherein at least a portion of the surfaces of said base portions and said spacer portion defining said channel being hydrophilic in character.

In accordance with the present invention, there is also provided a microplate comprised of a base and having a multitude of microholes or cavities and at least one cover placed in sealing relationship to said microholes or cavities and having a surface facing the interior of the microholes or cavities which is hydrophilic in character.

BRIEF DESCRIPTION OF THE DRAWINGS

FIG. 1a is a top view of a prior art lateral flow device.

FIG. 1b is a schematic diagram of the prior art lateral flow device of FIG. 1a;

DETAILED DESCRIPTION OF THE INVENTION

Figure 2:
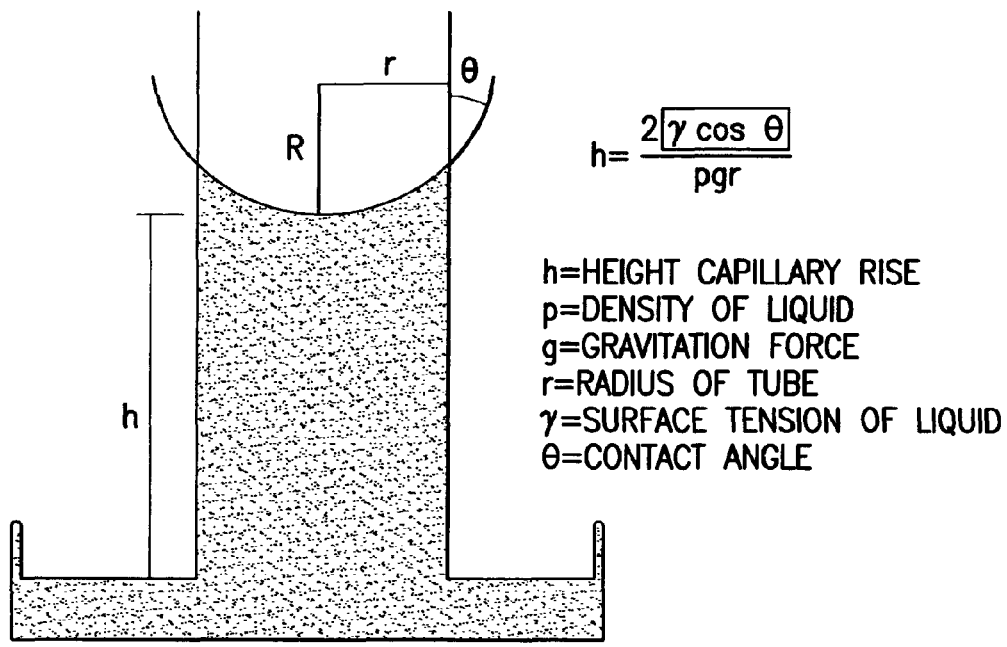
FIG. 2 is a depiction of capillary rise in a cylinder.

In accordance with the present invention, adhesives and polymer films may be formulated using polymer resins and surfactants to provide multifunctional bonding properties for use in in-vitro diagnostic devices.

Hydrophilic adhesives or films may be formulated to be thermally bonded or pressure sensitive. The hydrophilicity of the surface of the adhesive or film is controllable through the chemical structure, concentration and distribution of the surfactant in the adhesive coating. The hydrophilic properties reduce the surface tension of biological fluids (e.g., blood, urine, and sputum), thus allowing the rapid transfer of fluid from an inlet area to a remote reagent area in an in-vitro diagnostic device.

The invention will be described in connection with the Figures.

Lateral flow devices as shown in FIG. 1 typically have a sample inlet area for receiving the biological fluid. The sample inlet area or port may be proximal to a conjugate pad that holds reagents specific to the analytical test method. As the sample specimen flows from the inlet area through a reagent area, specific chemical reactions or a complex formation occur. The reaction product or complex continues to flow to a detection area where the analyte is monitored. Specimen fluids may continue to flow and be collected in an absorbent pad. The time required for determining the concentration of a specific analyte is dependent on the flow rate of the fluid and the reaction rate between the analyte and a specific test reagent.

Adhesive backings are typically used in the construction of lateral flow devices to support the various components of the device including the conjugate pad, a microporous membrane with specific reagents and an absorbent pad as shown in FIG. 1. The adhesive layer may be either pressure sensitive or heat-sealable, and may be present on a backing film such as a polyester film. The flow rate of the sample fluid is typically controlled by capillary flow through the microporous membrane.

Membranes used in lateral flow devices are typically hydrophobic polymers with low surface energy. These membranes are polymers such as nitrocellulose, nylon, polyether sulfone, polyvinylidiene, and the like. Consequently, these components are not compatible with aqueous biological fluids. To overcome the low surface energy of the membrane, surface active agents such as sodium dodecylsulfate (SDS) and sodium dodecylbenzene sulfonate (SDBS) are added to increase the wettability and consequent wicking ability of the membrane. Although the addition of surface active agents to the membrane increases its wettability these chemicals decrease the ability of the membrane to bond or retain proteins which may be critical to the analytical requirements and device performance. In addition, surfactants added to the membrane can reduce test sensitivity by reducing signal intensity due to extensive spreading of reagent bands.

It is known that the use of adhesives in diagnostic devices such as lateral flow devices to bond the hydrophilic membrane to the backing layer can result in a reduction in the effectiveness of the hydrophilic membrane layer during transport of the sample to be assayed across the membrane layer. Jones et al, *IVD Technology*, pp. 57-63, September, 2000. This reduced efficiency can be attributed to the migration of the adhesive into the membrane layer, creating isolated hydrophobic areas within the hydrophilic membrane. This effect is particularly enhanced upon use of an adhesive exhibiting low hardness (which exhibits high cold flow properties) in combination with a hydrophilic membrane of minimal thickness, thus enhancing the ability of the adhesive to affect the surface properties of the membrane. This effect can be minimized by the use of high hardness adhesives which exhibit low cold flow properties. However, high hardness adhesives also exhibit undesirable lower initial bond strength than a low hardness adhesive, a factor that must be taken into account when constructing the lateral flow device.

Strong intermolecular attractive forces exist between molecules to create surface tension. N. Vallespi i Salvado et al, "Surfactants in Pressure Sensitive Adhesives", *Surface Coatings International*, 4, 1999, pp. 181-185. These intermolecular forces create high surface tension in aqueous biological fluids such as blood, urine, and sputum. In comparison, the surface energy of solid substrates is low. This differential between the surface tension of biological fluid and substrates commonly used to make in-vitro diagnostic devices needs to be overcome to achieve lateral flow and wicking.

Two approaches can be used to improve the flow of biological fluids through a diagnostic device. One approach is to increase the surface energy of the substrate (or membrane) with various surface treatments. A second approach is to reduce the surface tension of the biological fluid.

Adhesives are typically hydrophobic polymers with a surface energy ranging from 30 to 40 dyne $cm^{-1}$. An approach to increase the flow properties of in-vitro diagnostic devices is to increase the surface energy of the hydrophobic adhesive coating. There are a number of patents that describe the synthesis and utility of hydrophilic polymers and adhesives.

For example, U.S. Pat. No. 3,686,355 describes a block copolymer of a base polymer with a second surface modifying additive. U.S. Pat. Nos. 5,354,815 and 5,614,598 describe polymers having enhanced hydrophilicity and thermal regulated properties. In this area, a hydrophilic polysiloxane anionic polymer is bonded to an aliphatic polyamide or polyester polymer fiber to enhance the hydrophilic and thermal properties of the textile. A number of U.S. and foreign patents are directed to the use of hydrophilic polymers used to formulate pressure sensitive adhesives. See, for example, U.S. Pat. No. 5,508,313 (hydrophilic pendant moieties on polymer backbone), U.S. Pat. No. 5,660,178 (hydrophilic crosslinking agents), U.S. Pat. No. 6,121,508 (lipophilic pressure sensitive adhesive with a surfactant for skin contact in biomedical electrodes), WO 00/56828 (use of hydrophilic ester monomers that are polymerized to produce a wet stick pressure sensitive adhesive), EP 869979B (preparation of hydrophilic pressure sensitive adhesive using polar monomers), U.S. Pat. No. 5,685,758 (hot melt adhesive with improved wicking for application to non-woven fabric), WO 97/48779 (hydrophilic hot melt adhesive composition prepared by blending adhesive components with a surfactant), and U.S. Pat. No. 6,040,048 (water removable pressure sensitive adhesive containing hydropilic pendent groups).

Polymeric films have modified surface properties are well known and produced by many distinct methods. See, for example, U.S. Pat. Nos. 2,502,841 (gaseous chlorine); 2,829,070 (halogen gas); 3,142,582 (acid bath); 3,326,742 (halogenated organic amine); 3,561,995 (reactive conditioning agent with metal ion); 3,843,617 (aqueous acidic solution); 3,968,309 (surfactant-containing curable coating); 4,190,689 (titanium dioxide treatment); 4,387,183 (grafting hydrophilic chains to polymer surface); 4,416,749 (irradiation and surface hydrolysis); 4,460,652 (grafted hydrophilic polymer coating); 4,595,632 (hydroxy-fluorocarbon graft surface treatment); 4,666,452 (surface modified by hydrogen sulfato groups); 5,273,812 (hydrophilic film of hydrophilic monomer together with surface active agent); 5,280,084 (surface modification with carboxyl, carbonyl and hydroxyl groups followed by reaction with heterocyclic compound); 5,332,625 (crosslinked polymer surface); 5,451,460 (coating of non-ionic, hydrophilic surfactant in binder); 5,503,897 (irradiation and alkalization of polymer surface).

The present invention is directed to the selection of multifunctional coatings, adhesives and films and their use in in-vitro diagnostic devices. Hydrophilic substrates or constructions can be hydrophilic heat seal coatings as well as pressure sensitive adhesive tapes. Pressure sensitive adhesive tapes facilitate device manufacturing and are integral to device performance. The combination of a pressure-sensitive or heat-sealable adhesive with hydrophilic properties to aid lateral flow and the wicking of biological fluids will prove beneficial to device manufacturers. Benefits will include increased flexibility in device design, increased wicking rates and consequently faster test results. Increased wicking consistency and potentially reduced sample volume are some of the advantages to be achieved through the use of hydrophilic pressure sensitive adhesives and heat-sealable coatings.

In view of the above, the objects of the present invention are to provide adhesive coatings or films with controllable hydrophilicity to increase the surface energy of the fluid flow path to enhance the flow of biological fluids in in-vitro diagnostic devices, provide hydrophilic adhesives that bond components of the diagnostic device thereby facilitating a more efficient manufacturing process for production of the device, increase the transfer rate of the sample fluid from an inlet port to distal reagents and therefore reduce the time for analysis, enable smaller sample volumes by enabling more efficient transport of fluid to a sensing reagent, and reduce risk of chemical interference by providing a wicking surface that allows an increased separation between the sampling port and the test reagents.

Hydrophilic coatings or films formulated by mixing surfactants with a polymer resin enhance the wicking of biological fluids into or through an in-vitro diagnostic medical device. Polymer resins may be selected from film forming polymers with a suitable glass transition temperature to form a hydrophilic coating. Similar resins may be selected for heat sealable hydrophilic coatings. In addition, resins typically used as pressure sensitive adhesives may be formulated with surfactants to provide a hydrophilic pressure sensitive adhesive. These constructions are dual functional in that they may serve to bond the components of the diagnostic device together and also to create high energy surfaces which reduce the surface tension of the biological fluid. The reduced surface tension of the fluid allows rapid transfer of the fluid from an inlet area to a remote reagent area in an in-vitro diagnostic device. The rapid fluid spreading can reduce the time needed for analysis. Since a smaller sample volume is required due to effective fluid wicking, device design flexibility is enhanced. This permits more efficient manufacturing processing with the potential for reduced product cost.

Hydrophilic coatings, films and adhesives can also be employed which do not require the incorporation of the surfactant into the formulation to provide the necessary hydrophilic properties. Examples of hydrophilic coatings and adhesives include polymers that can be cross-linked using di-hydroxyl terminated polyethylene glycol or polypropylene glycol monomers such as polyethylene glycol 600 supplied by Union Carbide Corporation. In addition, a vinyl terminated monomer with a hydrophilic moiety such as an anionic group can be grafted onto a polymer backing to increase the hydrophilic properties of the backing. One monomer that can be used is sodium AMPS, which is the sodium salt of 2-acrylamide-2-methyl-propanesulfonic acid, supplied by Lubrizol, which can be grafted onto the surface of a polymer by use of UV radiation. Such hydrophilic coatings can be used with and without the addition of a surfactant to provide a hydrophilic coating or adhesive.

Surface tension of a fluid is the energy parallel to the surface that opposes extending the surface. Surface tension and surface energy are often used interchangeably. Surface energy is the energy required to wet a surface. To achieve optimum wicking, wetting and spreading, the surface tension of a fluid is decreased and is less than the surface energy of the surface to be wetted. The wicking movement of a biological fluid through the channels of a diagnostic device occurs via capillary flow. Capillary flow depends on cohesion forces between liquid molecules and forces of adhesion between liquid and walls of channel. The Young/Laplace Equation states that fluids will rise in a channel or column until the pressure differential between the weight of the fluid and the forces pushing it through channel are equal. Walter J. Moore, *Physical Chemistry* $3^{rd}$ edition, Prentice-Hall, 1962, p. 730.

$$\Delta p = (2\gamma \cos \theta)/r$$

where $\Delta p$ is the pressure differential across the surface, $\gamma$ is the surface tension of the liquid, $\theta$ is the contact angle between the liquid and the walls of the channel and r is the radius of the cylinder. If the capillary rise is h and $\rho$ is the density of the liquid then the weight of the liquid in the column is $\pi r^2 gh\rho$ or the force per unit area balancing the pressure difference is $gh\rho$.

Therefore $(2\gamma \cos \theta)/r = gh\rho$ or $h = 2\gamma \cos \theta/g\rho$. For maximum flow through membranes (fluid wicking), the radius of the channel should be small, the contact angle $\theta$ should be small and $\gamma$ the surface tension of the fluid should be large.

Figure 3:
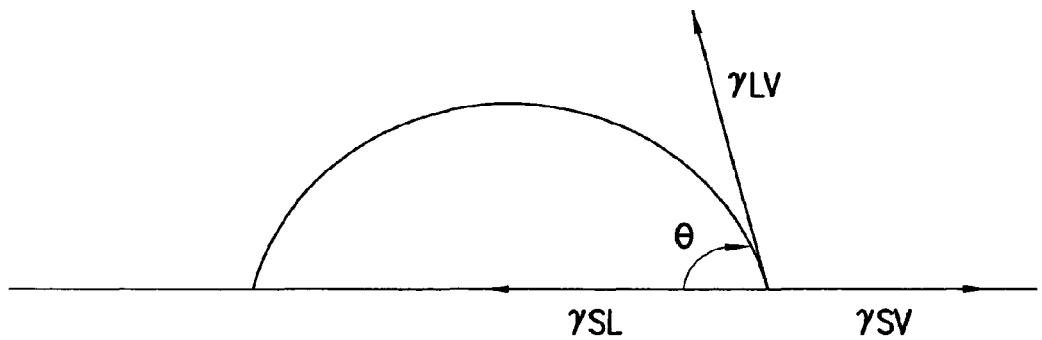
FIG. 3 is a depiction of the wetting of a fluid on a smooth flat surface.

Wetting is the adhesion on contact between a liquid and solid. W. A. Zisman, "Influence of Constitution on Adhesion", *Handbook of Adhesives*, $2^{nd}$ edition, Van Nostrand Reinhold Co., 1977, p. 38. For maximum wetting, the surface tension of the liquid must be less than or equal to the surface tension of the solid surface. This is the critical wetting tension of the solid. FIG. 3 illustrates surface wetting of a fluid on a flat smooth surface.

The theoretical explanation of this phenomenon can be described by the classical model know as Young's Equation. T. Young, *Philos. Trans. Roy. Soc.* London, 95 (1805) p. 65.

$$\gamma_{SV} = \gamma_{SL} + \gamma_{LV} \cos \theta \qquad \text{Eq. 1}$$

The diagram shown in FIG. 3, illustrates the relationship between the contact angle $\theta$ and surface tension of liquid $\gamma_{LV}$ and solid $\gamma_{SV}$. W. A. Zisman, ibid, pp. 33-64. When the contact $\theta$ between liquid and solid is zero or so close to 0, the liquid will spread over the solid.

The spontaneous process of wettability can also be derived from the differential between work of adhesion and cohesion by substitution of Dupre Equation below in Equation 2:

$$W_A = W_C = \gamma_{SV} + \gamma_{LV} - \gamma_{SL} - 2\gamma_{LV} = \gamma_{SV} - (\gamma_{LV} + \gamma_{SL}) \qquad \text{Eq. 2}$$

This equation implies that spontaneous spreading will occur if the work required separating the liquid-solid interface is greater than liquid separation itself. Therefore, Equation 2 can be further derived by introducing the initial spreading coefficient S defined by Harkins ("The Physical Chemistry of Surface Films", Reinhold, 1952) and shown in Equation 3 below:

$$S = W_A - W_C = \gamma_{SV} - (\gamma_{LV} + \gamma_{SL}) \qquad \text{Eq. 3}$$

Since $\gamma_{SL}$ is relatively small in comparison with $\gamma_{LV}$, the initial spreading coefficient term becomes:

$$S = \gamma_{SV} - \gamma_{LV} \qquad \text{Eq. 4}$$

Spreading is the movement of liquid across a solid surface. Contact angle is a measure of wettability. Spreading increases as the contact angle decreases until wetting is complete. Hence, the spreading will occur spontaneously when S is greater than zero, which also indicates that the surface tension of the solid must be greater than that of the liquid, as shown in Equation 4. From the initial spreading coefficient equation showed above (Eq. 4), the wettability will occur either by increasing surface tension of the solid or decreasing surface tension of liquid.

Surface treatments can be used to increase the surface energy of a solid include both physical and chemical methods. Corona discharge, mechanical abrasion, flame and plasma treatment are techniques used to increase surface energy. P. H. Winfield et al, "The Use of Flame Ionization Technology to Improve the Wettability and Adhesive Properties of Wood", *Int'l Journal of Adhesion and Adhesives*, Vol. 21(2), 2001. Chemical surface treatments include cleaning, priming, coating and etching to change the surface energy. Corona discharge treatment is the most widely used technique for surface treatment of plastics. During the treatment, the plastic surfaces are heavily bombarded with oxygen radicals at high-energy radiation levels. Consequently, the plastic surface either undergoes electret formation (J. M. Evans, *J. Adhesion*, 5(1973) pp. 1-7) or chemical structural changes (J. M. Evans, *J. Adhesion*, pp. 9-16; D. K. Owens, *J. App. Polymer Science*, 19(1975), pp. 275-271 and 3315-3326). Either proposal will improve the wettability of plastics. Another commonly used method is wet chemical treatment. This treatment involves oxidizing the plastic surface through exposure to oxidizing acids such as a mixture of chromic acid and sulfuric acid. (D. Briggs et al, *Journal Material Science*, 11 (976))

Six commonly used industrial plastics were selected for study. General information for each plastic is listed in Table 1:

TABLE 1

General Information for Selected Plastics

| Plastic & Abbreviation | Product Name | Manufacturer |
| --- | --- | --- |
| Polypropylene (PP) | Amoco Polypropylene | Amoco Chemical Company |
| High Density Polyethylene (HDPE) | Petrothene HD 5003C | Quantum Chemical Corporation |
| Polycarbonate (PC) | Cyrolon UVP PC | Cyro Industries |
| Polyethylene terephthalate (PET) | Rynite | Du Pont |
| Poly methyl methacrylate (PMMA) | Acrylite | Cyro Industries |
| Acrylonitrile-butadiene-styrene terpolymer (ABS) | Cycolac GPX3700-1000 | GE Plastics |

Each plastic was treated using two methods: 1) corona discharge and 2) chromic acid. The corona discharge treatment involved exposing the surface of each plastic to an electric discharge of 10,000 to 50,000 volts at a frequency of approximately 500 kilohertz for approximately 5 seconds. The chromic acid treatment required the plastic surface to be flooded with chromic acid for 15 seconds then the acid was removed by washing with distilled water then rinsing the surface with isopropanol then wiped dry. The contact angle was measured immediately after drying or corona treatment using the method described below. The contact angle was measured on each plastic to quantitatively determine the effect of each treatment on the surface energy.

Figure 4:
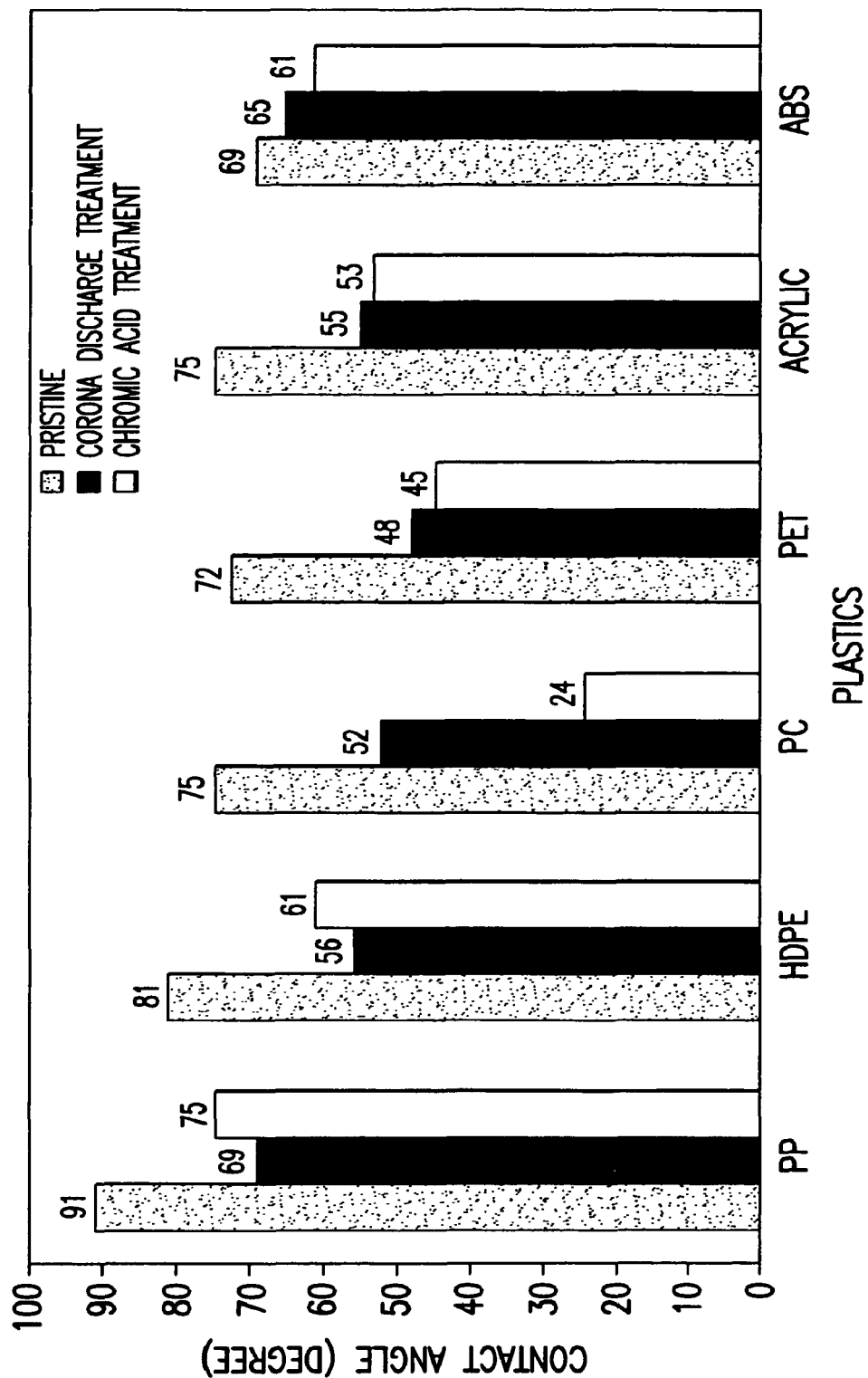
FIG. 4 graphically depicts the effect of surface treatment on contact angle.

The data in FIG. 4 shows that water contact angles on treated plastics decrease indicating an increase in surface energy. Consequently, the wettability of biological fluids will also be enhanced as a result of these treatments. Both corona discharge and chromic acid treatments were effective in improving the wettability of the surfaces. Corona discharge was most effective in increasing the surface energy of the polyolefin films (PP and HDPE) while chromic acid was more effective on plastics with more reactive groups such as polycarbonate and polyester panels. The corona discharge treatment method could improve the water contact angle by orienting surface electrical charges or by introducing oxygen on the surface. Either mechanism will increase the polarity of the plastic and thereby increase its surface tension. Consequently, the contact angle θ will be smaller due to reduced difference in surface tension between the plastic $\gamma_{SV}$ and the water $\gamma_{LV}$. A disadvantage of corona discharge treatment is the instability of the treatment. Corona treated substrates should be coated soon after treated.

The use of surfactants to lower the surface tension of a fluid is well known. M. J. Rosen, *Surfactant and Interfacial Phenomena* John Wiley & Sons, New York, (1978); Th. F. Tadros, *Surfactants*, Academic Press, Inc. New York, (1984); A. C. Clark et al, "New and Improved Waterborne Systems", *Adhesives Age*, September (1999), 33-40.

The effect of surfactants in coatings and adhesives has been studied to determine their effect on wettability, fluid flow rate and adhesive properties. Each surfactant was formulated into a base adhesive at different concentrations. The water contact angle was measured to determine the effect of surfactant on reducing the surface tension of the water.

TABLE 2

Physical Properties of Selected Surfactants

| Chemical Description | Structure | Charge Types | Mol. Wt. |
|---|---|---|---|
| Sodium 2-Ethylhexyl Sulfate | Branched | Anionic | 232 |
| Sodium Lauryl Sulfate | Linear | Anionic | 288 |
| Sodium Nonylphenol Ether Sulfate | Aromatic | Anionic | 498 |
| Nonylphenol Ethoxylate | Aromatic | Nonionic | 704 |
| Polyalkyeneoxide Modified Heptamethyltrisiloxane | Linear Siloxane | Nonionic | 600 |

Hydrophilic coatings and heat-sealing and pressure sensitive adhesives were prepared. Dissolution of polymeric resins occurred in organic solvents. Dissolution was followed by measurement of solution solids and viscosity over a period of several hours.

The surfactant was introduced into the liquid polymer mixture after dissolution of the resin. Gentle agitation for several minutes was sufficient to achieve homogeneity. Hydrophilic pressure-sensitive formulations were prepared by the introduction of a surfactant into liquid acrylic adhesive solutions and emulsions followed by gently mixing until dispersed or dissolved.

Figure 5:
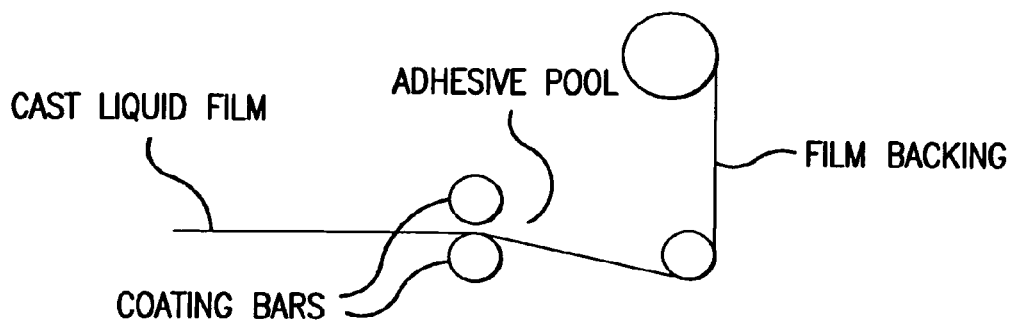
FIG. 5 depicts a laboratory coating technique for casting adhesive on a film.

Hydrophilic films were prepared in the lab using coating apparatus. The lab preparations were accomplished by use of coating bars that evenly spread the liquid formulations on a film backing as shown in FIG. 5. The liquid adhesive was first deposited as a pool onto a film backing, then the backing drawn through two stainless steel bars until the adhesive solution spread across and down the film to produce an even coating thickness. The thickness of the film was controlled the gap set between the two coating bars. The cast films were dried for five to ten minutes in a Blue M Stabil Therm convection oven set at 105° C. The dried coatings had an approximate thickness of 0.0005 to 0.001 inches, as measured with a Mitutoyo Absolute Digital Thickness Gage. The hydrophilic adhesive coatings were protected with a film substrate of low surface energy (release liner).

The hydrophilic coatings were tested for surface wetting using de-ionized water. The sessile drop method was employed to measure the contact angle liquid water makes with the surface of the hydrophilic thin film. A ramé hart contact angle goniometer was used.

A micropipette was used to draw deionized water from a beaker. Several drops of the liquid were dispensed back into the beaker to ensure a bubble free liquid. The micropipette was then mounted onto the goniometer.

An approximate 1"×1" sample of hydrophilic film was place on the goniometer stage with the hydrophilic surface towards the drop. The film was flattened then secured to the stage by placing a magnet or clamps on each side of the film. Gloves were used when handling the film surface to avoid any oils or dirt from hands that could alter the surface of the film.

Figure 6:
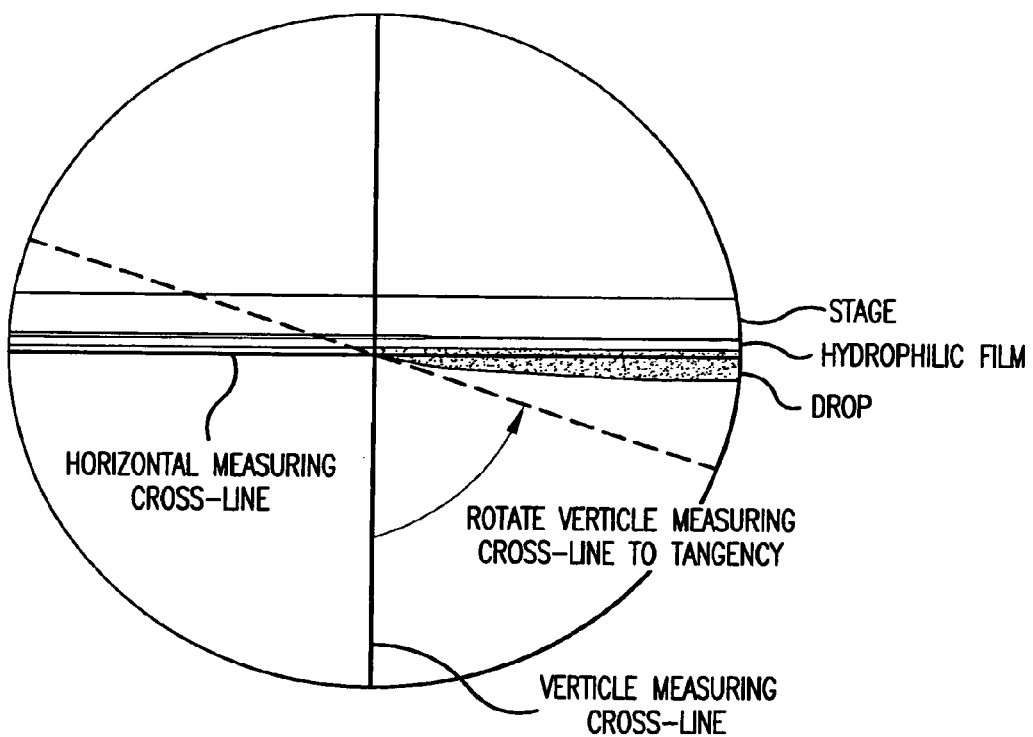
FIG. 6 depicts a method for contact angle measurement on a flat surface.

The micropipette was then lowered to just above the hydrophilic surface. A drop of water with a volume of approximately 2 μl was suspended on the tip and lowered towards the film until the water drop dispensed onto the surface. The drop of water was allowed to spread across the surface until equilibrium was established (30 seconds). The microscope was focused to view the extreme left or right of the resulting drop (see FIG. 6). The cross-line inside the scope was adjusted to tangency above the base of the drop to create a wedge of light bounded by the two cross-lines and the drop profile. The cross-line was slowly rotated while adjusting the cross travel of the specimen stage assembly so that the wedge of light is gradually extinguished and the cross-line attains tangency with the drop profile at the base of the drop. The contact angle was read directly from the scope reticle at the six o'clock position. The contact angle was recorded to the nearest degree on both sides of the spread water drop.

Samples of the hydrophilic pressure sensitive and hydrophilic heat seal adhesive substrates were tested for peel adhesion to stainless steel panels. Testing was performed on a MTS Alliance RT/1 mechanical tester equipped with a 25-lb load cell and hydraulic grips. The machine was interfaced with a Dell Optiplex GX1p computer system containing MTS TestWorks software package and Hewlett Packard 895c printer.

The hydrophilic pressure sensitive adhesive tapes were tested for peel strength from 6"×6" stainless steel panels using Adhesives Research ART 1005, "Five Minute Peel". The method is similar to ASTM D3330-83. The testing was carried out in a controlled temperature (70° F.) and humidity (50% RH) environment. Prior to testing, the stainless steel panels were cleaned with high purity urethane grade 2-butanone. The tape samples were cut to 1"×10", then laminated (two passes) to the stainless steel panel using a 4.5-lb, 80 durometer hardness roller. Peel testing was initiated after a five-minute dwell, by attachment of stainless steel plate to the bottom set of grips and overhanging, unbound portion of tape to the top set of grips. The tape was pulled away from the stainless steel plate at a rate of 12 inches/minute and at an angle of 180-degrees. The load and displacement were observed to increase to a maximum over the first 1-inch of the test then remain constant until the test was complete. The peel strength was calculated from the quotient of average load (oz) between one and five-inch displacement on the panel, and the sample width (in).

Hydrophilic heat seal coatings were tested for adhesion using ASTM D1876-95. The testing was carried out at 70° F. and 50% relative humidity. Adhesion was tested after lamination to a cleaned 7-mil polyester film. The samples were heat laminated on a Wabash press by exposure for 2 seconds at 100° C. and at a pressure of 30-40 psi. The samples were aged four days at 70° F. and 50% R.H. Peel testing was conducted as described above and found to be acceptable.

Figure 7:
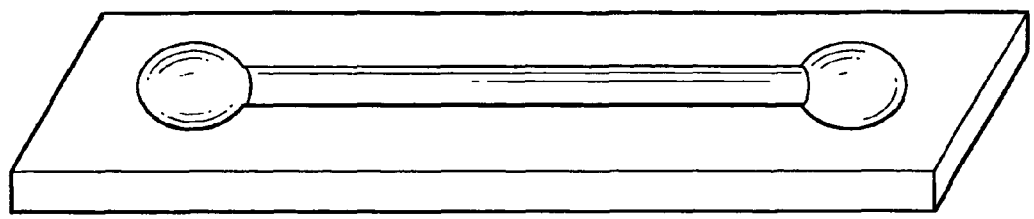
FIG. 7 depicts a microfluidic device used in in-vitro sample analysis.

The effect of hydrophilic coatings and adhesives on the flow rate of distilled water in a microfluidic channel was investigated. Following a screening of the effect of different types of surfactants on contact angle, the most effective surfactants were formulated into adhesive tapes that were used as a cover for a microfluidic device as shown in FIG. 7.

The microfluidic channel was molded in a device made from polystyrene. The channel had a length of 20 cm with a depth of 10 microns and a width of 30 microns. The hydrophilic tape was used to close the channel to create the microfluidic device. Distilled water was placed in one of the terminal wells and the time for the water to flow through the channel was measured.

Chemical surface analysis of the hydrophilic coatings was performed using infrared spectroscopy via attenuated total reflectance (ATR). The spectra were recorded using a Pike Miracle ATR single bounce sample port unit using a ZnSe crystal. Film samples were compressed onto the crystal using the compression arm at full contact pressure. Infrared spectra were collected using a MIDAC M1300 Series FT-IR bench with a mercury-cadmium-telliuride (MCT) nitrogen cooled detector. Absorbance spectra were collected from 30 scans per sample from 4000 $cm^{-1}$ to 600 $cm^{-1}$ at 2 $cm^{-1}$ resolution at a gain of 1×. The FTIR bench was interfaced with YKE Microsystem computer and analyzed using Grams 32 software package.

The surface topography of the hydrophilic coatings was observed using atomic force microscopy. The instrument used was a Digital Instruments Nanoscope IIIa Multimode instrument. Hydrophilic tapes were mounted onto 1-cm diameter magnetic stubs and imaged in the tapping mode. Using this mode, the AFM cantilever is oscillated at its resonant frequency. Contact between the oscillating tip and the tape surface causes a decrease in the measured amplitude of oscillation. Since the contact is made at the largest displacement from the cantilever equilibrium position, little energy is transferred to the sample and minimal deformation of the sample occurs. Images were obtained by raster scanning the sample surface under the tip and recording the z motion of the sample necessary to maintain constant amplitude during the scan. This mode of imaging has several advantages over direct contact mode imaging. Lateral forces that are prevalent during contact mode scans are eliminated. Additionally, this tapping mode provides a non-destructive method for the imaging of soft samples. Importantly, phase images obtained using the tapping mode can give additional information concerning the mechanical and adhesive properties of the sample surface. A. Doring et al, "Atomic Force Microscopy: Micro- and Nano-Mapping of Adhesion, Tack and Viscosity", $23^{rd}$ *Annual Technical Seminar: Pressure Sensitive Adhesive Tapes for the New Millennium*, May, 2000, pp. 213-222.

All samples were initially scanned in air. The hydrophilic coating HY-10 was then rinsed with de-ionized water for 10 seconds before being wiped dry with a paper tissue. The sample was left to dry overnight and imaged the next morning.

Figure 8:
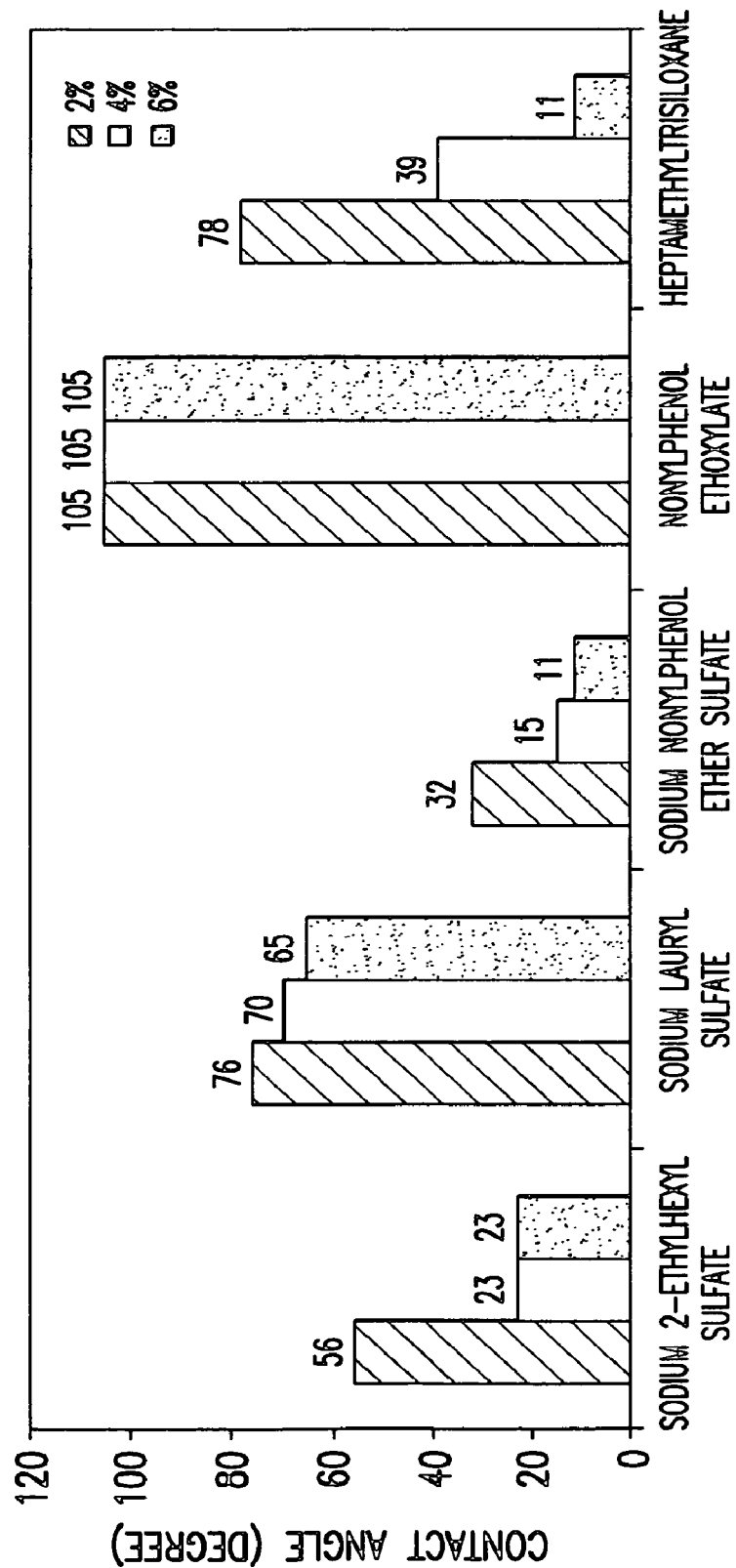
FIG. 8 depicts the effect of surfactant concentration on contact angle.

Various surfactants as shown in Table 2 were formulated into an emulsion pressure sensitive adhesive. FIG. 8 shows that most test samples exhibit a similar trend of decreasing contact angle with increasing surfactant concentration. Sodium nonylphenol ether sulfate exhibited the most effective surface tension reduction of water at all three surfactant concentrations used in this study. The nonionic surfactant, nonylphenol ethoxylate, exhibited little effect on the contact angle of de-ionized water. This may be due to its higher molecular weight and the lower water affinity of the hydrophilic group compared to anionic type surfactants. In addition, the nonylphenol group enhances its absorption onto the polymer surface. Polyalkyeneoxide modified heptamethyltrisiloxane (PMHS) (SIILWET L77 from Union Carbide), also a non-ionic surfactant, reduced the water contact angle of the adhesive surface compared with the nonylphenol ethoxylate. PMHS has a siloxane polymer backbone instead of a hydrocarbon backbone, which accounts for its lower surface energy. In addition, PMHS also has a lower molecular weight than nonylphenol ethoxylate which enhances its mobility within the adhesive matrix. PMHS can be formulated into a solvent-based pressure sensitive adhesive in amounts of up to about 20% by wt. to increase the hydrophilic properties of the adhesive.

Of the surfactants evaluated, sodium nonylphenol ether sulfate had the highest molecular weight of the anionic surfactant used. It is believed that the lower molecular weight anionic surfactants have better solubility into the adhesive matrix so that the concentration of the surfactant at the water/adhesive interface is less. The linear structure of sodium lauryl sulfate may improve its solubility into the adhesive so that its effect on the adhesive surface is less than that of sodium 2-ethylhexyl sulfate.

Figure 9:
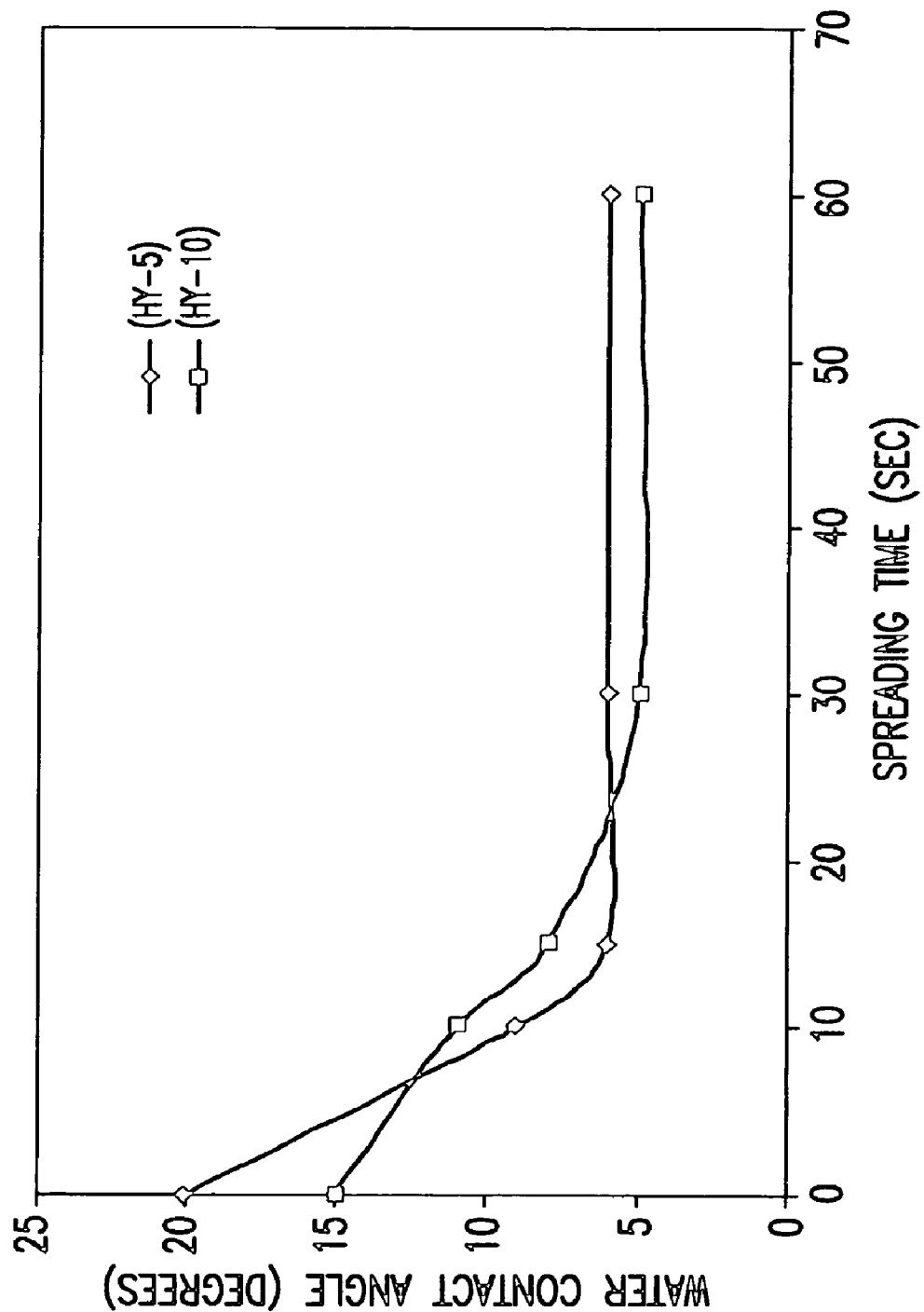
FIG. 9 depicts water contact angle vs. spreading time for hydrophilic films.

The wetting of the surface of HY-5 and HY-10 which are two hydrophilic heat seal adhesives was investigated by measuring the spreading of water. These hydrophilic heat seal adhesives were formulated using polyester resins and the anionic surfactants, sodium nonylphenol ether sulfate and sodium dioctylsulfo succinate, respectively. FIG. 9 is a graph that describes the spreading behavior of water on the surface of HY-5 and HY-10 thin film coatings. Water was dropped onto the surface of the adhesives and the contact angle was measured as a function of time. Initially there is rapid spreading of the drop as it contacts the surface of the film. The contact angle decreases quickly to less than 10 degrees. Equilibrium is established within thirty seconds to one minute. This spreading behavior is typical of the hydrophilic coatings, heat-seal adhesives, and pressure sensitive adhesives.

Figure 10:
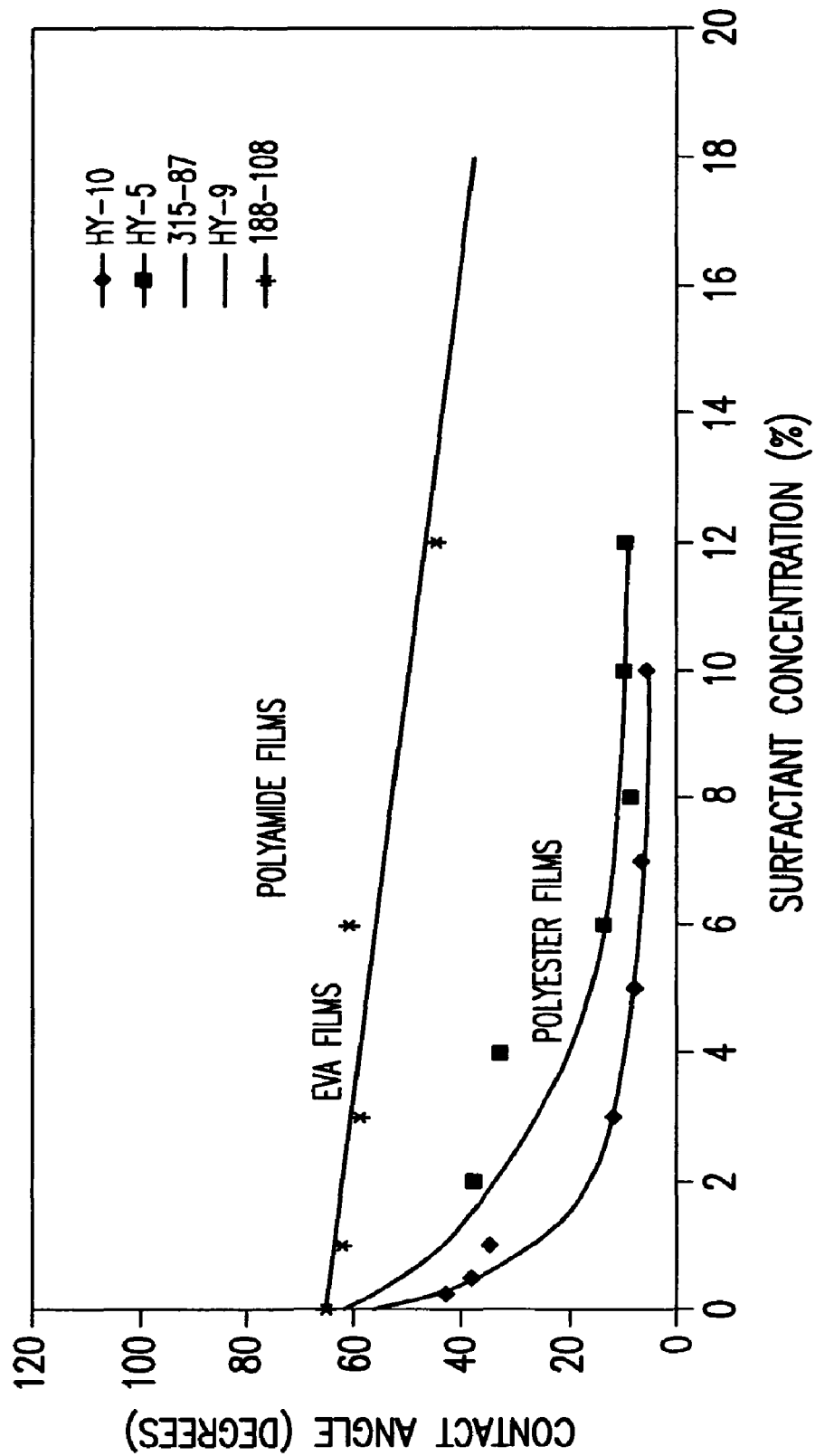
FIG. 10 depicts water contact angle vs. surfactant concentration for films.

FIG. 10 shows the effect of the surfactant concentration on the surface wettability of the dried films prepared using different polymeric resins. Polyamide, ethylene vinyl acetate, and polyester resins were formulated with sodium dioctylsulfo succinate. The resins studied included films of polyamide, ethylene vinyl acetate, and polyester chemistries. When no surfactant is present in the coatings the contact angle is high since the polymeric resins are hydrophobic. By increasing the surfactant concentration the surface becomes more hydrophilic and lower water contact angles are observed indicating significant surface wetting. At very high surfactant concentrations the wetting effect can be enhanced or attenuated depending on the surfactant and its compatibility with the polymer matrix.

Figure 11:
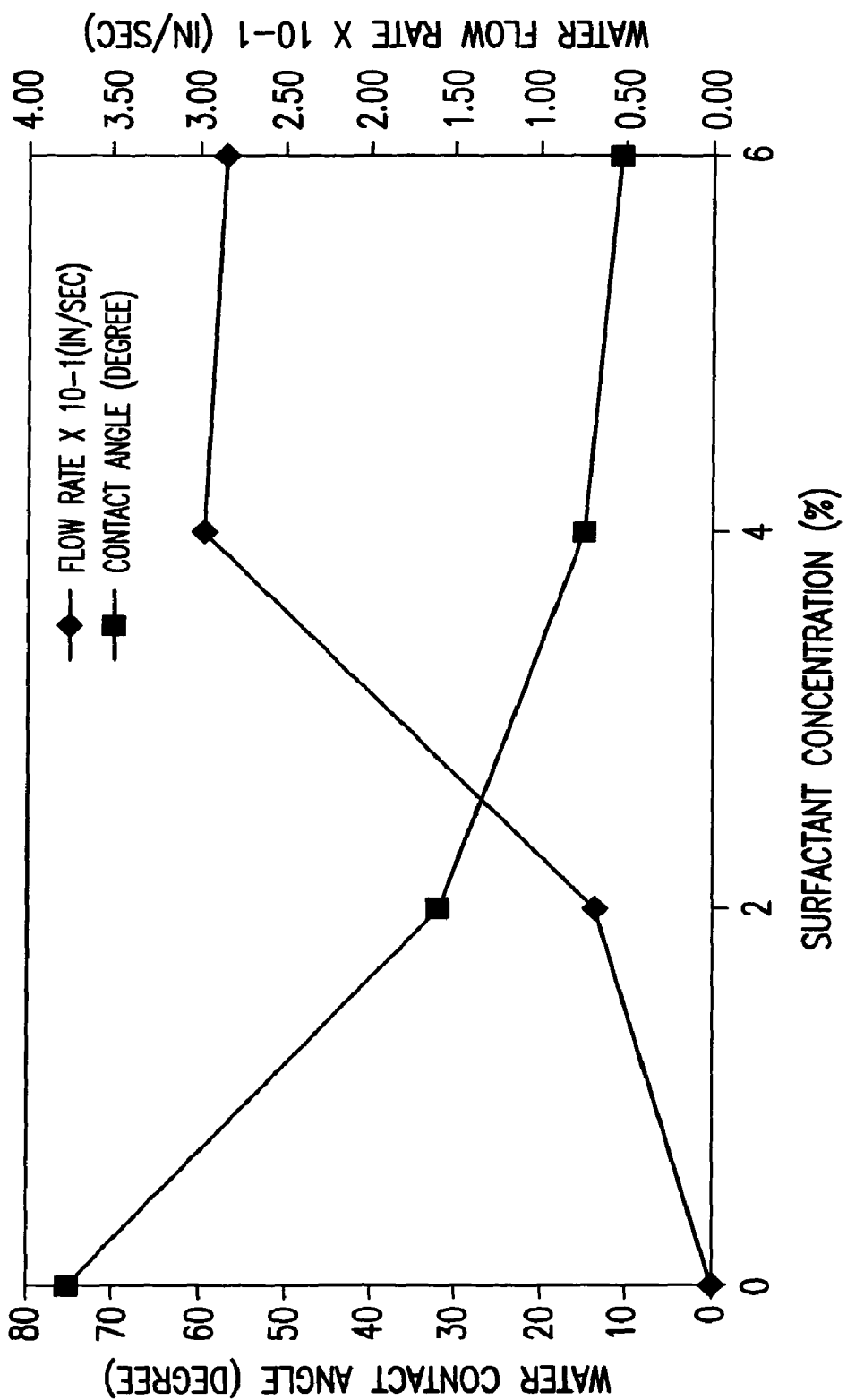
FIG. 11 depicts the effect of surfactant concentration on contact angle and flow rate.

FIG. 11 shows the effect of surfactant concentration on the rate of water flow in a covered microfluidic device (corresponding to device of FIG. 7). In this experiment, a hydrophilic pressure sensitive adhesive was formulated using concentrations of sodium nonylphenol ether sulfate ranging from 0 to 6 percent. When there was no surfactant added to the adhesive, water did not flow through the channel. With increasing concentration of surfactant the rate of water flow through the microchannels increased while the contact angle decreased.

The increased flow rate of water can be attributed to the reduction of water surface tension. The principle that could be used to explain this phenomenon is capillary rise as shown in FIG. 2 which documents the relationship between the surface tension and the contact angle. The height of the water in the capillary is determined by a factor of two times the product of liquid surface $\gamma_{LV}$ and cos θ regardless of liquid density and gravitation force. As a result, the water will advance further when the surface tension of water is close to the surface tension of the capillary material that is now determined by the hydrophilic adhesive cover. At high surfactant concentration (greater than 4% in FIG. 11), the rate of flow levels off since the concentration of surfactant exceeds the critical micelle concentration. Additional surfactant on the surface of the adhesive does not reduce the surface tension of the fluid and may become autophobic. W. A. Zisman, "Influence of Constitution on Adhesion", *Handbook of Adhesives*, $2^{nd}$ edition, 1977, p. 46.

Atomic force microscopy (AFM) was used to visualize the topography of a hydrophilic coatings. The AFM images of coatings containing 0%, 1%, 5% and 10% surfactant were obtained. The images show enrichment of the film surface at the film/air interface with increasing amount of surfactant introduced to the adhesive formula. The AFM image of the coating containing no surfactant shows a relatively smooth, flat surface.

Transformation is observed when 1% or less surfactant has been incorporated into the adhesive coating, where raised surface features are observed on the film surface. Increased surface topography is observed at 5% surfactant while at 10% surfactant the surface appears to be smoother due to saturation of the surface.

Infrared spectra of the coatings confirm the increase in surfactant concentration on the surface. The prominent peak at 2958 $cm^{-1}$ in the ATR is assigned to the C—H stretch of a $CH_3$ group on the surfactant in the hydrophilic adhesive and is used to monitor surfactant accumulation on the surface. A plot of absorbance of the C—H stretch as a function of concentration of surfactant at 0%, 1.0%, 5.0% and 10% shows a flattening resulting from the surface saturation by the surfactant.

Hydrophilic coatings, hydrophilic pressure-sensitive and heat-sealable adhesives may be used in a variety of in-vitro diagnostic devices, including capillary flow, lateral flow, microfluidic, microtiter plates and electrophoretic devices.

The following are examples of various embodiments of the present invention:

EXAMPLE 1

Hydrophilic Coating

A polyester resin with a high glass transition temperature commercially available as Vitel 2200 BA from Bostik Chemical Company is dissolved in a solvent of methyl ethyl ketone and toluene (7:3 weight ratio). A commercial surfactant such as Rhodapex CO-436 available from Rhodia Inc. is dissolved in the resin solution to provide a surfactant solids to resin ratio of between 3:97 to 6:94. A hydrophilic coating is formed by spreading the resin/surfactant solution onto a polymer film and allowing the solvent to evaporate. Wetting the dried film surface with distilled water causes spreading of water on the surface. The contact angle of the water on the surface ranges from 5 to 10 degrees.

EXAMPLE 2

Hydrophilic Heat Sealable Coating

A similar formulation and coating as in Example 1 is prepared using a polyester resin with a lower glass transition temperature such as Vitel 3200 through 3500 series resins with a glass transition temperature between −15° C. to +15° C. One example is Vitel 3300B which has a Tg of +11° C. A heat sealable hydrophilic coating is formed by coating the formulation of resin and surfactant onto a surface such as a polymeric film and allowing the solvent to evaporate. The contact angle of the hydrophilic coating is similar to those of Example 1 (5 to 10 degrees). Other resins such as ethylene vinyl acetate and polyamide polymers may be used as heat sealable formulations.

EXAMPLES 3-8

Hydrophilic Pressure Sensitive Coatings

Aqueous Based

A hydrophilic pressure sensitive coating is prepared by formulating an emulsion based resin such as Aroset 3500 available from Ashland Specialty Chemical Company (division of Ashland, Inc.), with a surfactant such as Rhodapex CO-433 available from Rhodia, Inc. The formulation was coated onto a hydrophobic polymer film such as 5 mil polyester film available from DuPont Teijin Films. After coating and drying the formulation, the contact angle was measured. The following table illustrates the effect of surfactant concentration on the contact angle which is related to the surface energy of the hydrophilic adhesive. The adhesive 180° peel force can be modified through addition of additives such as tackifiers.

| Acrylic Resin (%) Aqueous Solvent | Rhodapex CO-433 (%) | Contact Angle (Degrees) | 180° Peel (oz/inch) |
|---|---|---|---|
| 99 | 1 | 95 | |
| 98 | 2 | 32 | 68 |
| 97 | 3 | 29 | |
| 96 | 4 | 15 | 6 |
| 95 | 5 | 13 | |
| 94 | 6 | 11 | 7 |

EXAMPLES 9-12

Hydrophilic Pressure Sensitive Coatings

Solvent Based

Similar to Examples 3-8, hydrophilic pressure sensitive adhesive coatings are formulated using solvent based adhesives and surfactants. An acrylic resin adhesive in the organic solvent ethyl acetate was formulated with various concentrations of Rhodapex CO-433. After coating onto a polyester film and drying, the contact angle of the coating was measured. The following table shows the effect of surfactant concentration on the contact angle and 180° peel force.

| Acrylic Resin (%) Ethyl Acetate Solvent | Rhodapex CO-433 (%) | Contact Angle (Degrees) |
|---|---|---|
| 97 | 3 | 33 |
| 94 | 6 | 17 |
| 91 | 9 | 16 |
| 88 | 12 | 15 |

In addition to the concentration of the surfactant, the surface energy of the hydrophilic coating can be controlled by the selection of surface active agent. The selection of surface active agent is based on factors such as molecular weight, linear vs. branched structure, ionic vs. non-ionic and the type of ionic moiety present, aromatic vs. aliphatic structure, etc. These chemical structure properties can be used to control the hydrophilic characteristics and surface energy of the coating. The following table shows the effect on contact angle of 2 percent surfactant in Aroset 3500 coatings by the selection of surfactant structure. The following table shows the effect of surfactant characteristics on coating wettability:

| Surfactant/ Contact Angle | Ionic Charge | Molecular Wt | Structure |
|---|---|---|---|
| Sodium 2-Ethylhexyl sulfate 41° | anionic | 232 | branched |
| Sodium octyl Sulfate 19° | anionic | 232 | linear |
| Sodium lauryl Sulfate 20° | anionic | 288 | linear |
| Sodium Nonylphenol sulfate 32° | anionic | 382 | aromatic |
| Nonylphenol Ethoxylate 105° | nonionic | 820 | aromatic |

A novel feature of using a hydrophilic coating formulated with Rhodapex CO-436 (the ammonium salt of sulfated nonylphenol ethoxylate) is the ability to pattern the surface energy of a uniform coating using radiant energy. When thermal energy is applied to the coating in a pattern such as stripes, circles or any other configuration, the surface energy in the area of applied energy is reduced. It is believed that ammonia gas is evolved due to the thermal energy leaving the sulfonic acid of nonylphenol ethoxylate remaining. The hydrophilicity of the coating decreases and consequently becomes water resistant. Radiant energy sources such as lasers and electron beam may also be employed to cause the evolution of a labile cation to customize the physical character of the coating. This may be used with advantage in the production of in-vitro diagnostic devices, such as by the application of thermal energy to the surface to produce a parallel, laterally-oriented, striped pattern of alternating hydrophilic/hydrophobic areas. The presence of the hydrophobic areas may be employed with advantage to slow the wicking of the material to be tested as it travels from a hydrophilic region to a hydrophobic region, whereby additional time for reaction between the analyte and the reagent results. Fluid wicking through the device may be retarded over areas of lower surface energy to permit time for reaction or complex formation by use of a single coating. This may be employed to avoid too rapid fluid wicking which may be detrimental if the reaction time is insufficient. Of course, a series of reaction zones of various shapes and configurations can be created on a single film.

Figure 13:
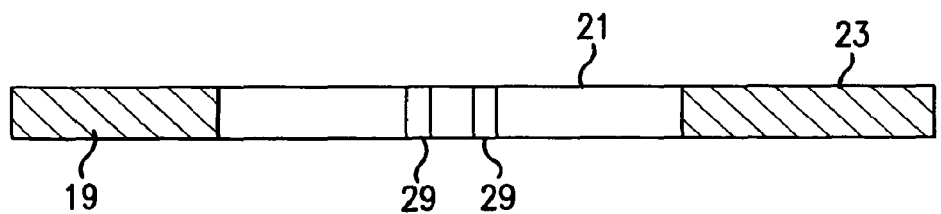
FIG. 13 is a top view of the lateral flow diagnostic device of FIG. 12.
Figure 14:
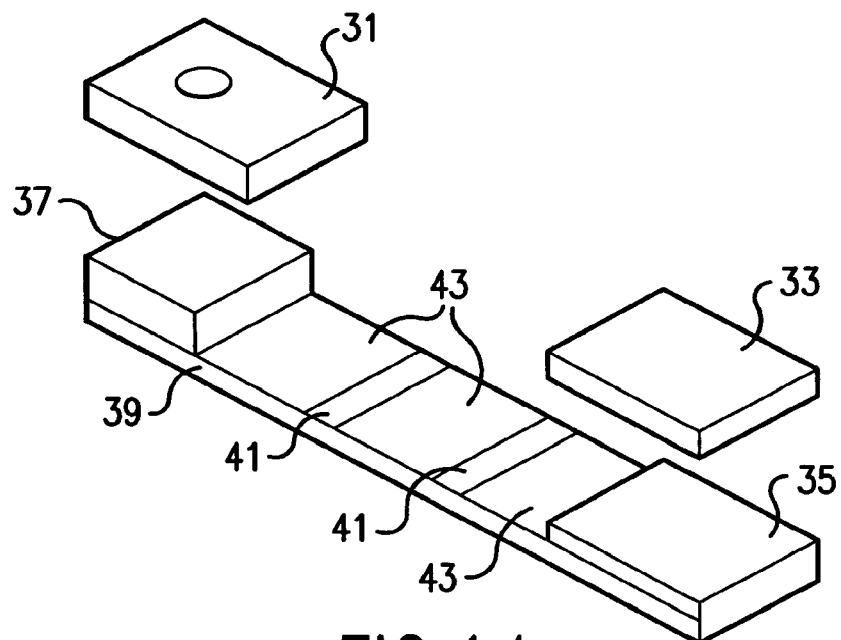
FIG. 14 is an exploded view of a lateral flow diagnostic test strip of the present invention.
Figure 15:
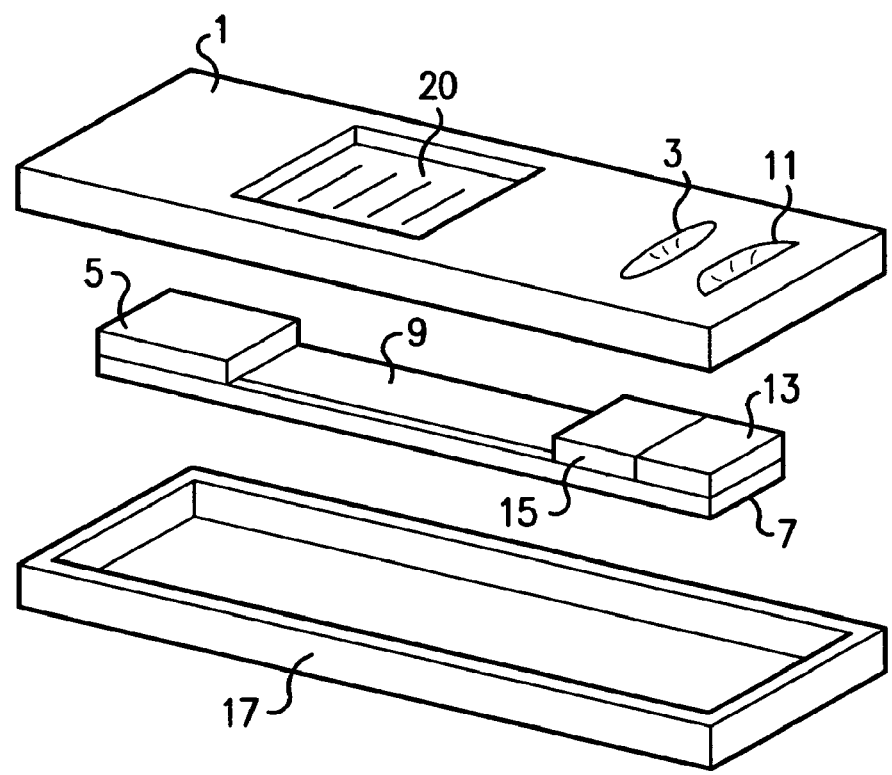
FIG. 15 is an exploded view of another embodiment of a lateral flow test strip of the present invention.

The present invention may be employed with advantage in a variety of in-vitro diagnostic devices, both of the lateral flow and of the capillary flow type, with devices of the lateral flow rate type of FIGS. 12-17. In one embodiment of a lateral flow device of the present invention as depicted in FIG. 15, the device comprises a housing cover 1, means (port) 3 in the housing to introduce a sample to be assayed into the device, means 5 (absorbent pad) for fluid collection, and a backing strip 7 having spaced apart first and second ends. The means for sample fluid collection is adhered to the backing at a first end of the backing strip, the means to introduce the sample is adhered to the backing at the second end of the backing strip. A microporous or porous membrane 9 is optionally placed between the first and second ends to provide an avenue for travel of the sample between the first and second ends as well as to provide a matrix for any reagent material that may be present for contact with the fluid sample, during which time the sample contacts the reagent with which reaction or contact is to occur.

Advantageously, in accordance with the present invention, the surface of the backing strip between the first and second ends is hydrophilic in character. The backing strip 7 may be, e.g., heat-sealable or exhibit pressure sensitive adhesive properties. If the backing strip 7 exhibits pressure sensitive adhesive properties, the hydrophilic character of the material serves to avoid reducing the effectiveness of any membrane 9 attached to the backing strip in the event that migration of the adhesive into the membrane occurs.

By way of further advantage, due to the hydrophilic character of the backing strip, it may be possible to avoid use of the membrane 9, instead relying solely on the hydrophilic character of the backing strip itself to wick the sample from the sample introduction point to the sample collection point. In such an embodiment, the reagent with which the sample must contact or react with will either be applied directly to the backing strip for contact with the sample, or be introduced to the surface of the backing strip from a reservoir attached to the backing strip in a conventional manner.

Port 11 may be employed to provide access for another material such as a buffer to be applied to absorbent pad 13. The sample once added to port 3 contacts absorbent pad 15. The assembly of the backing strip and associated attached components may be positioned within a bottom portion 17 of the housing. The housing cover 1 includes view port 20 for viewing the visual result of the reaction between the sample and the reagent present in the device.

Figure 12:
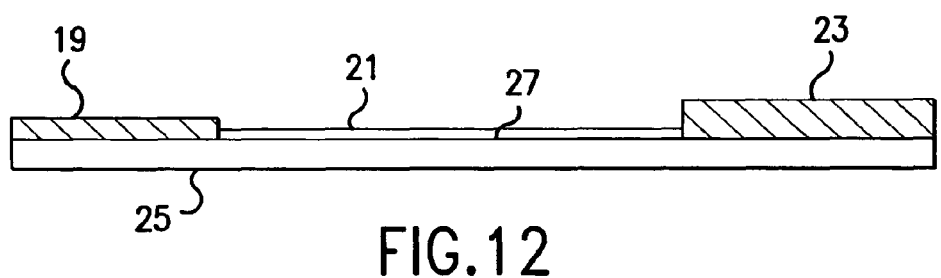
FIG. 12 is a side view of a lateral flow diagnostic device of the present invention.

FIGS. 12 and 13 depict a lateral flow test strip according to the present invention. The test strip includes sample absorbent pad 19, membrane 21 and sample collection pad 23. Backing strip 25 includes a hydrophilic surface 27 which may be heat-sealable or pressure sensitive in nature in accordance with the present invention. Areas 29 on the membrane 21 contain reagents for reaction with the sample. Alternatively, the membrane may be omitted and its function served by the hydrophilic surface of the backing strip 25. In such an embodiment, the areas 29 may still contain reagents for reaction with the test sample, and areas 29 of the backing strip may also be made more hydrophobic (or less hydrophilic) than the remaining surface of the backing strip. The presence of such areas will serve to slow the rate of passage of the sample across the backing strip to maximize time of contact with the reagents in areas 29.

Another embodiment of the device of the present invention is depicted in FIG. 14. The device of FIG. 14 includes covers 31,33 for the respective ends of the device, which include sample pad 37 and collection pad 35, with test zones 41 being intermediate the ends of the device on backing strip 39 having a hydrophilic surface 43. As discussed above, test zones 41 may be positioned on portions of the backing strip which have been rendered less hydrophilic (or more hydrophobic) than the remaining portion of the backing strip.

Various modifications can be undertaken with advantage in such an embodiment. As discussed above, selective areas of hydrophilic/hydrophobic surface character can be provided on the surface of the backing material to modify the flow characteristics of the fluid sample, either by directing the sample longitudinally along the backing strip toward the fluid collection point, or by causing the fluid sample to contact adjacent hydrophilic/hydrophobic areas to slow the flow rate of the fluid sample along the backing strip. In such an instance, for example, the reagent may be placed on the hydrophobic portion where the wicking of the fluid sample would be slower to permit a longer contact time with between the fluid sample and the reagent. In terms of this discussion, the term hydrophobic is not intended to mean that the portion of the backing would be entirely hydrophobic, but could also mean that that the area is more hydrophobic than the adjacent hydrophilic portion of the backing strip (i.e., both portions would have varying degrees of hydrophilicity so that the wicking of the fluid sample would still be encouraged to travel from the sample inlet to the sample collection area).

Accordingly, in the context of FIGS. 12-15, the surface of the backing film (e.g. a polyester film as in FIG. 1) could be rendered hydrophilic by any of the methods discussed above, and employed as a heat-sealable layer for bonding to the absorbent pad and the sample pad/conjugate pad. Optionally, a c membrane could also be bonded to the heat-sealable hydrophilic backing strip. Alternatively, the use of the membrane can be avoided and the reagents applied directly to the hydrophilic surface of the backing strip and the sample and reagent caused to wick directly across the surface of the backing strip toward the absorbent pad.

As discussed above, in an embodiment where the backing strip comprises a hydrophilic pressure sensitive adhesive layer, the membrane can still be used with advantage due to the hydrophilic character of the adhesive without fear of diminishment of the ability of the membrane to function due to migration of the adhesive. However, it is still possible to avoid the use of the membrane, with the hydrophilic adhesive layer serving as the transport medium for the sample from the sample pad to the absorbent pad. Any reagents desired to be contacted with the sample may be applied directly to the surface of the hydrophilic adhesive layer. The adhesive character of the backing strip can also be employed with advantage to bond the respective sample/conjugate/absorbent pads to the backing strip. This facilitates the manufacture of the device. Such a device would typically be contained in a suitable housing that generally includes a viewing window to determine the extent of the reaction of the sample and the reagent (e.g., to determine extent of reaction due to color formation or the intensity of the color formed).

Figure 16:
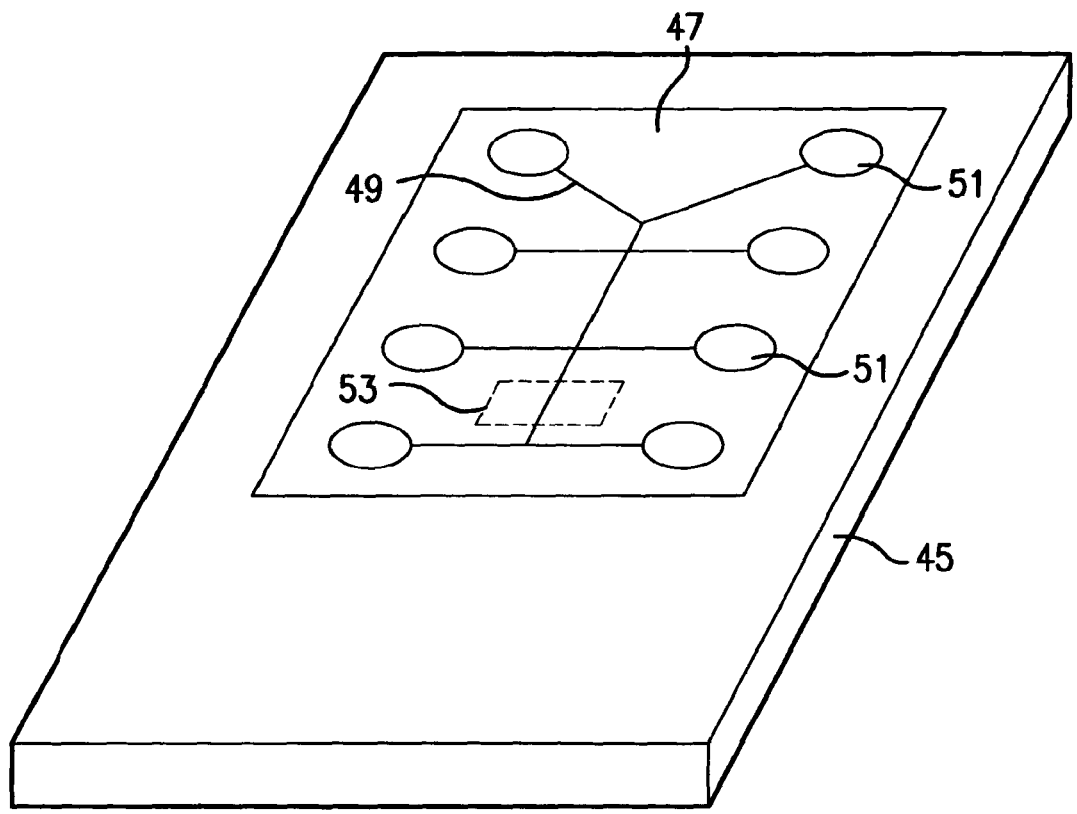
FIG. 16 is a view in perspective of a microfluidic diagnostic device according to the present invention.

In the context of a microfluidic diagnostic device which employs capillary transport of the fluid sample during the analysis procedure, such devices typically include microfluidic channels molded in a suitable polymeric substrate (see FIGS. 7 and 16). Microfluidic devices generally refers to a device having one or more fluid channels, passages, chambers or conduits which have at least one internal cross-sectional dimension (width or depth) of between 0.1 um and 500 mm within which a fluid sample passes from an inlet port to a detection zone.

The microfluidic diagnostic device is generally comprised of a substantially planar base portion having one or more microfluidic channels, passages, chambers or conduits therein. A variety of materials may comprise the base portion, including polymeric materials such as polymethylmethacrylate, polycarbonate, polytetrafluoroethylene, polyvinylchloride, polydimethylsiloxane, polysulfone, and silica-based substrates such as glass, quartz, silicon and polysilicon, as well as other conventionally-employed substrate materials.

Such substrates are manufactured by conventional means, such as by injection molding, embossing or stamping, etc. The microfluidic passages or channels may be fabricated into the base portion by conventional microfabrication techniques known to those skilled in the art, including but not limited to photolithography, wet chemical etching, laser ablation, air abrasion techniques, injection molding, embossing, and other techniques. The base material is selected on the basis of compatibility with the desired method of manufacture as well as for compatibility with the anticipated exposure to materials and conditions, including extremes of pH, temperature, salt concentration, and the application of electric fields. The base material may also be selected for optional properties including clarity and spectral characteristics.

An enclosure surface or cover is placed over the top portion of the base substrate to enclose and otherwise seal the microfluidic passages or channels. In the context of the present invention, the channels or passages are covered with a substrate according to the present invention the surface of which is hydrophilic which covers the passages or channels in the base substrate. The fact that the surface of the covering substrate is hydrophilic in nature enhances the flow of the liquid through the microfluidic passages and channels. As discussed above, the hydrophilic covering substrate can comprise a variety of types of materials having hydrophilic character, such as a hydrophilic pressure sensitive adhesive layer, a hydrophilic heat-sealable layer, a hydrophilic surface-treated layer, etc. Hydrophilic pressure sensitive adhesives can be bonded to the upper portion of the base substrate in covering/sealing relation to the microfluidic passages/channels by application of pressure. Hydrophilic heat-sealable layers can be bonded to the upper portion of the base substrate in covering/sealing relation to the microfluidic passages/channels by application of pressure and heat, with the temperatures employed being sufficient to cause bonding of the covering layer without adversely affecting the physical structure of the base material. Other means of bonding the covering material to the base substrate can be employed such as acoustic welding techniques, UV curable adhesives, etc.

Such devices typically include optical detector means positioned adjacent to a detector window whereby the detector senses the presence or absence of an optical characteristic from within the microfluidic passage or channel resulting from flow of the liquid sample through the passage or sample. The optical detector may comprise any of a variety of detector means such as fluorescent, calorimetric or video detection systems, which include an excitation light source (laser or LED), etc. A variety of optically detectable labels can be employed to provide an optically detectable characteristic such as colored labels, colloid labels, fluorescent labels, spectral characteristics and chemiluminescent labels.

As discussed above, an alternative to otherwise having to ensure that the channels possess sufficient hydrophilicity to cause the fluid sample to travel along the capillary tube, the top portion of the channel is covered with a hydrophilic material in accordance with the present invention. That is, a heat-sealable polymeric film having hydrophilic surface characteristics may be applied over the open cavity of the channel to both enclose the channel and provide the necessary hydrophilic character so that the fluid sample will be caused to wet the channel. As an alternative, the polymeric film may include a pressure sensitive adhesive coating which is also hydrophilic in character to provide the necessary hydrophilicity to cause the fluid sample to wet the channel. The use of such materials in the construction of the microfluidic diagnostic device also serves to simplify the manufacturing of the device. In the context of the present invention, the entire facing surface of the covering layer need not be hydrophilic; instead, only that portion of the covering layer that serves to enclose the microfluidic channels or passages is required to be hydrophilic. Of course, as is the case with lateral flow devices, certain portions of the covering layer that enclose the microfluidic channels or passages may be rendered less hydrophilic than other portions to modify the flow rate of the fluid sample.

Figure 17:
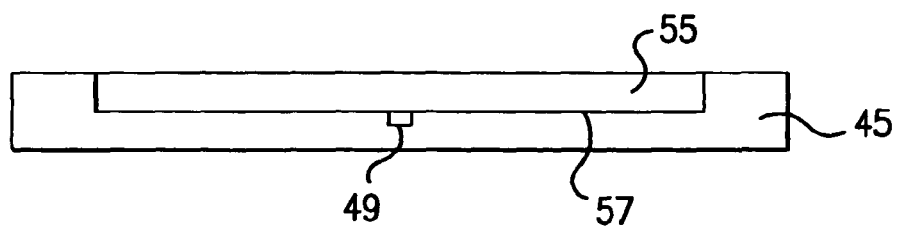
FIG. 17 is a cross-sectional view of the device of FIG. 16.

A typical microfluidic device which has been prepared in accordance with the present invention is depicted at FIGS. 16 and 17. The device of FIG. 16 includes base portion 45, recess 47 in the top of the base 45, open microfluidic channels 49, fluid reservoirs 51 and viewing window 53. In the device of FIG. 16, the microfluidic channels 49 are uncovered in order to depict the interior of the device. In the cross-sectional view of the device of FIG. 16 (at FIG. 17), base portion 45 includes microfluidic channel 49 which is shown to be enclosed by cover portion 55. Cover portion 55 includes a facing hydrophilic surface 57 whereby the fluid sample which enters the microfluidic channel 49 will contact the facing hydrophilic surface and cause the sample to be transported along the length of the channel. The facing surface 57 of the cover 55 may be rendered hydrophilic by various means in accordance with the present invention, such as by the presence of a hydrophilic pressure sensitive adhesive, by the rendering of the surface of the cover itself hydrophilic by suitable means such as by mechanical or chemical treatment, etc. For example, cover 55 may be heat-sealed or adhesively attached to the interior portion of the base 45.

Figure 18:
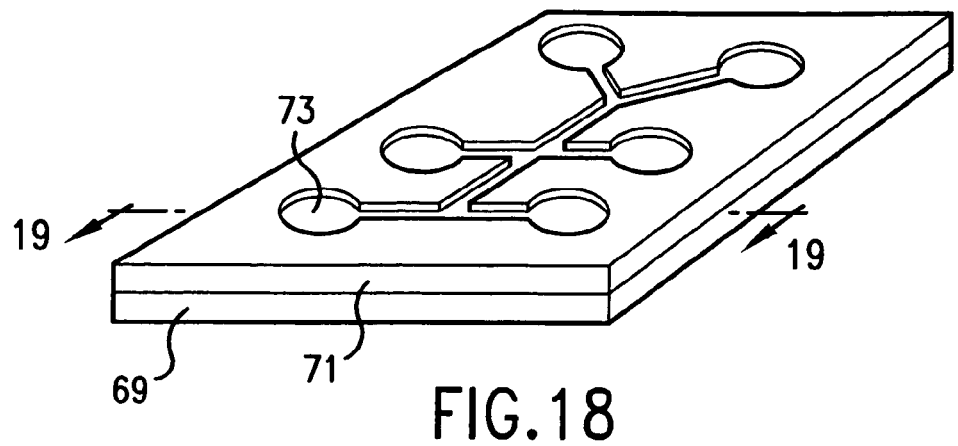
FIG. 18 is a view in perspective of another embodiment of a microfluidic device having an adhesive spacer portion attached to a base portion.
Figure 19:
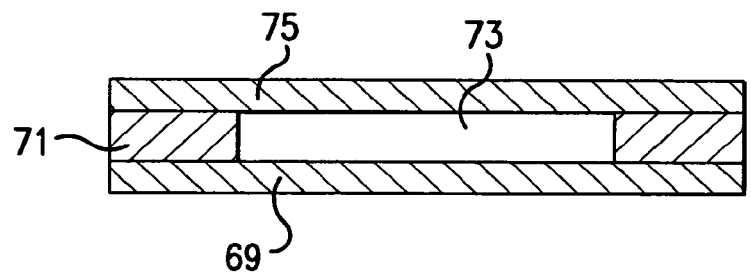
FIG. 19 is a view in cross-section of the microfluidic device of FIG. 18 wherein both base portions are present.

By way of an alternative embodiment depicted in FIGS. 18 and 19, the microfluidic in-vitro diagnostic device may be comprised of opposing base layers 69, 75 separated by an adhesive spacer layer 71. While only a single base layer is shown in FIG. 18 so as to depict the fluid channels 73, both base layers are shown in FIG. 19. The spacer layer 71 may have fluid channels 73 provided therein within which a fluid to be assayed passes from a reservoir to a collection point. At least a portion of the surfaces of the base layers 69, 75 and the spacer layer which define the boundaries of the fluid channels are hydrophilic in character. The requisite hydrophilic character may be provided in several ways. For instance, one or both of the base layers 69, 75 or the adhesive layer may be hydrophilic or rendered hydrophilic by any of the methods described herein. For example, the respective layers may be comprised of a polymeric material which is inherently hydrophilic, rendered hydrophilic as a result of a compounding step, or surface treated to provide the necessary hydrophilicity. The spacer layer 71 preferably is an adhesive layer which is bonded to the opposing base layers, either as a result of pressure sensitive adhesive properties of the spacer layer or as a result of being heat-sealed to each of the base layers. If pressure sensitive, the spacer layer may be used in the form of a transfer film or as a double face construction. As discussed above, if the base layers are not hydrophilic in character, the spacer layer would possess the requisite hydrophilic character to assist wetting of the fluid channel by the fluid sample. The fluid channels 73 in the spacer layer may be die-cut into the spacer layer or provided by any other means effective to provide a spacer layer with the requisite fluid channels. One advantage of such a construction is that the micro-fluidic device may be constructed easily without the need to mold the fluid channels into the base layers as in the embodiment of FIG. 16.

Figure 20:
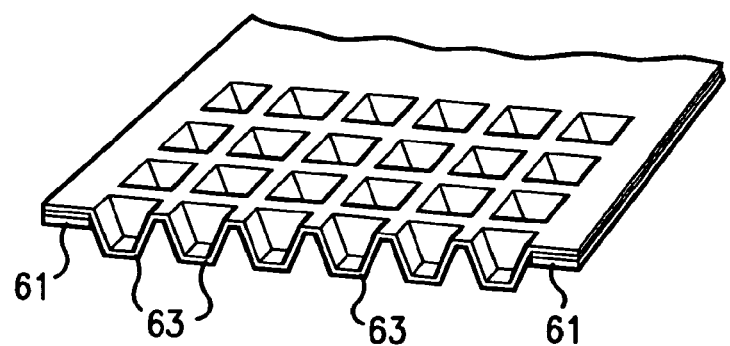
FIG. 20 is a view in perspective of a micro plate without a cover sheet.
Figure 21:
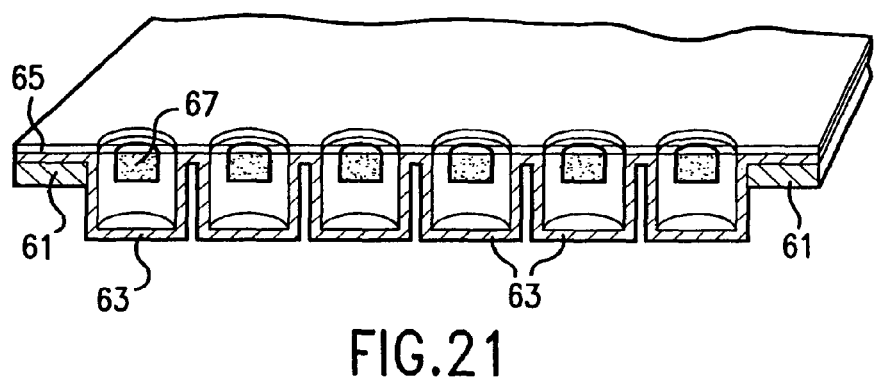
FIG. 21 is a view in perspective of the micro plate of FIG. 18 with a cover sheet.

Microplates of the present invention include various embodiments such as microwell-containing microplates as shown in FIGS. 20 and 21. As shown in the Figures, the microplate includes base portion 61 within which are formed a multitude of microwells 63. The microwells 63 may be of any suitable configuration, such as hexagonal or cylindrical as depicted. FIG. 20 depicts the presence of a cover plate or sheet 65 on the top of the base portion 61 to seal the microwells. The cover plate or sheet may comprise a heat-sealable film or may have pressure sensitive properties. As depicted in FIG. 20, a suitable material such as a lyophilized substrate, etc. may, as desired, be attached to the the inner surface of the cover plate or sheet in the event that the inner surface of the plate or sheet exhibits pressure sensitive adhesive properties, or by use of other adhesive means. In the context of the present invention, the cover plate or sheet, at least on the inner surface thereof which covers the microwells, will exhibit hydrophilic properties. Such properties can be provided by use of a pressure sensitive adhesive which is rendered hydrophilic in the manner taught above, or by use of a heat sealable film which is similarly possesses hydrophilic properties also in the manner taught above.

Figure 22:
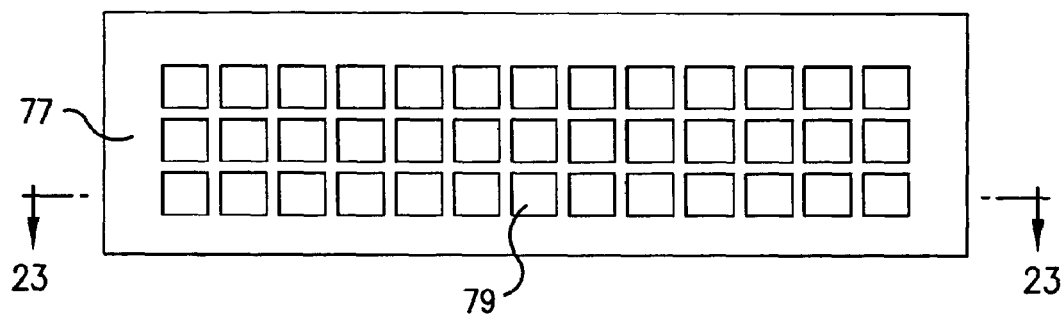
FIG. 22 is a top view of an open well microplate having a multitude of holes therein.
Figure 23:
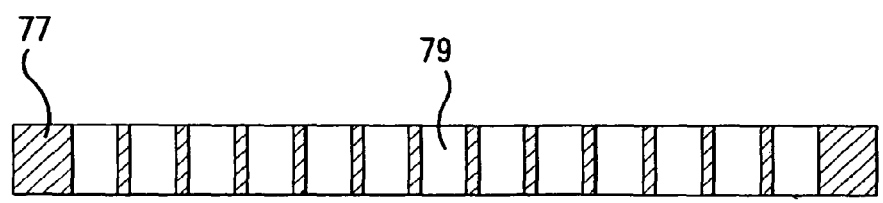
FIG. 23 is a view in cross-section of the open well microplate of FIG. 22.

An alternative microplate embodiment is shown in FIGS. 22 and 23 which comprises an open well microplate having a base portion 77 containing a plurality of microholes 79 cut or molded therein and passing completely through the base portion 77. The base portion 77 would be provided with facing cover plates or layers in order to seal the respective microholes 79 so that the respective liquid samples may be placed therein. Either or both of the base portion or the cover portions (not shown) adjacent the holes would be rendered hydrophilic in character. The covering plates or layers may be attached to the base plate by suitable adhesive means such as pressure sensitive adhesive or heat sealable adhesive properties of the cover plates or layers.

The present invention may employ a polymeric film which has been surface modified to exhibit hydrophilic properties. Polymers which can be modified in this manner are well known in the art. Exemplary of such polymers are the following polymers: polyolefins, including but not limited to polyethylene, polystyrene, polyvinyl chloride, polyvinyl acetate, polyvinylidene chloride, polyacrylic acid, polymethacrylic acid, polymethyl methacrylate, polyethyl acrylate, polyacrylamide, polyacrylonitrile, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, ethylene-vinyl acetate copolymer, polycarbonate, ethylene-isobutyl acrylate copolymer, as well as random or block copolymers of two or more polyolefins or a polyolefin and a non-olefin. Similarly, blends of two or more polymers may also be employed, as long as the polymer produced is hydrophobic in character.

The polymer may also comprise a polyester such as polyethylene terephthalate, polyethylene isophthalate-terephthalate, copolymers of poly-(1,4-cyclohexane dimethylene) terephthalate, poly(1,4-cyclohexane dimethylene) isophthalate, and isophthalate-terephthalate copolymers; poly(1,4 phenylene) terephthalate and isophthalate and copolymers; poly(1,4-phenylene)-4,4'diphenyl dicarboxylate; polyesters derived from aliphatic dibasic acids, such as maleic, adipic and sebacic acids and polyhydroxy compounds such as polyethylene glycol, neopentyl glycol, butylene glycol, glycerol, pentaerythritol, and cellulose. Preferably, the film-forming polymers used in the present invention exhibit a Tg or Tc sufficient to permit the polymer to be film-forming as well as to enable the resulting polymer film to be heat sealable at a sufficiently low temperature (e.g., in the range of from 70 to 100° C.).

As discussed above, a variety of surfactants may be admixed with the polymer to render the surface of the polymer hydrophilic. Surfactants which are suitable for use in the present invention include any surfactant which effectively imparts hydrophilic surface properties to the hydrophobic polymer film. While the identity of such surfactants is not critical to the practice of the present invention, anionic surfactants are preferred. However, exemplary of such surfactants (without limitation) are ammonium salts or sodium salts of alkyl phenoxy (polyethylene oxy) ethanol, ammonium perfluoroalkyl sulfonates, etc. Exemplary surfactants preferably include one or more hydroxyl, carboxylic acid, sulfonic acid, and amine functionalities. A detailed discussion of surfactants resides in Kirk-Othmer, *Encyclopedia of Chemical Technologies*, $2^{nd}$ Edition, Vol. 19, pages 512-564, herein incorporated by reference.

The above embodiment of the present invention may be practiced as follows in order to result in the formation of a hydrophobic polymer film having hydrophilic surface properties. Initially, a hydrophobic film-forming polymer is admixed with a suitable solvent to form a solvated solution of the polymer in the solvent. The polymer is admixed and dissolved in the solvent under conditions which permit the polymer to be so dissolved. Such conditions may include, for example, temperatures within the range of from 20 to 30° C., although higher temperatures may also be employed depending upon the polymer and solvent employed. The solvent which is employed is dependent upon the selection of the particular polymer. Exemplary solvents from which such selection may be made include but are not limited to toluene, methyl ethyl ketone, xylene, ethyl acetate, tetrahydrofuran, methylene chloride, n-heptane, n-butylacetate, acetone, cellosolve acetate, methyl cellosolve, n-butanol, isopropanol, n-propanol, and ethanol.

Once so formed, the solution of the polymer and the polymer solvent is admixed with a suitable surfactant which is soluble within the solution of the polymer and the polymer solvent. The surfactant is admixed in an amount of, for example, up to about 10% by weight, based on the total weight of the polymer and surfactant. Preferably, the surfactant is admixed with the polymer in an amount in the range of from about 3 to 6% by weight.

Once the mixture of polymer, solvent and surfactant is formed, the mixture is cast or otherwise caused to be formed into a film. The solvent contained in the thus-formed film is then caused to be removed from the film by the application of heat or other means (such as by reduced pressure). The film which then results is comprised of a hydrophobic polymer which exhibits desirable homogeneous hydrophilic surface properties. For example, an elevated temperature within the range of about 80° C. to 120° C. may be employed depending upon the vaporization temperature of the solvent. It is not advisable to employ a temperature much in excess of the vaporization temperature of the solvent in order to avoid loss of homogeneity of the hydrophilic surface properties exhibited by the resulting film.

It is frequently a disadvantage in any determination by means of fluorescent detection that "background" fluorescence occurs which may affect the accuracy of the desired fluorescent detection. It has previously been proposed to employ "low background" assay platforms and well plates for use in fluorescent detection methods to minimize the degree of background fluorescence during the assay. See U.S. Pat. Nos. 5,910,287 and 6,171,780 in this regard. These patents teach the use of polymers having low fluorescence and high transmittance such as cycloolefins in the formation of the bottom portion of the wells in a multi-well assay platform.

It would be desirable, however, to also employ a low fluorescent sealing or cover layer either alone or in conjunction with a low fluorescent assay platform or multi-well plates to further reduce the possibility of undesirable background fluorescence during the assay by fluorescent detection.

Fluorescence is defined as "radiative transition from the lowest excited singlet state ($S_1$) to the ground state ($S_o$) (*Electronic Properties of Polymers*, ed. J. Mort et al, p. 177, 1982). Materials for applications where no or minimal fluorescence is preferred (such as microfluidic devices) typically have high excitation energy potential. In polymeric materials, the base monomer preferably has a high ionization potential and low electron affinity. High energy is required to excite the molecules from a ground state to an excited state. Low fluorescent compounds do not easily accept charge transfer from other compounds or excited states. Similarly, molecules that are easily polarized by the delocalization of an electron should be avoided. Aromatic compounds and compounds with a conjugated pi electron structure may be easily excited by a radiate excitation source due to their non-localized electrons.

Advantageously, such sealing or cover layers will exhibit low natural fluorescence at the excitation and detection wavelength used to detect the biomaterial; will be dimensionally stable and not flow into any microfluidic channels present; will adhere to the base plate without creating voids or gaps that may allow migration of the components from one channel to an adjacent channel; is compatible with the chemical reagents used in the microchannels and reservoirs such as electrophoretic media and biomaterials including DNA fragments and polypeptides; be compatible with the separation conditions employed including pH (e.g., pH of 2-12, preferably 3-8), electric field potentials and voltage gradients of 200 volts/cm; exhibit good stability to moisture and temperature change; preferably contain no charged substituents which may interfere with the separation of biomaterials that contain charged groups; contain no leachable components that may contaminate the sample; and exhibit little or no spectral emission in the wavelength range of 400 to 800 nM. Such sealing or cover layers may possess pressure sensitive adhesive properties or be heat sealable.

With respect to the material used in the assay platform, such material may be either flexible or rigid, but is preferable that such materials be clear and colorless; chemically compatible with electrophoretic separation; exhibit little or no fluorescence under assay detection conditions as evidenced by little or no spectral emissions in the wavelength of 400 to 800 nM; be dimensionally stable and withstand pressure during electrophoresis; and dissipate heat during electrophoresis; and have minimal cross-sectional dimension.

When the sealing layer comprises a pressure sensitive adhesive or is a polymeric layer which adheres to itself, it is preferable to use a liner to protect the sealing surface. If a liner is used, it is desirable that there is no transfer of compounds from the liner to the sealing surface which will interfere with the separation of biomaterials or increase the fluorescence of the sealing surface.

Materials suitable for use in the present invention which exhibit minimal or low fluorescence and which may be used as substrate materials include but are not limited to polyolefins, polysiloxanes, polyalkylmethacrylates, and polycarbonates. Examples of suitable substrate films include Rohm PLEXIGLASS S30K, Rohm OROGLASS, and Goodfellow Polymethylmethacrylate and Mitsubishi SKINKOLITE HBS 007.

Materials suitable for use in the present invention as sealing or cover materials which exhibit minimal or low fluorescence include but are not limited to the above materials as well as adhesives such as alkyl(meth)acrylic acid esters. Preferred adhesive compositions contain no aromatic moieties such as those found in aromatic solvents, aromatic monomers, polymerization inhibitors or polymerization initiators as the presence of the aromatic moiety will result in undesirable spectral emissions. If any aromatic solvents such as toluene or xylene are used in the formation of the adhesive, they are removed during the drying process or by subsequent treatment of the product. Silicone-based adhesives such as Dow 7657 or Sylgard 184 (polydimethyl siloxane) may also be used. A low fluorescence sealing layer may be provided with advantage comprised of amorphous polyolefins such as polyethylene, polypropylene or blends of polyolefins.

Preferred acrylate-based pressure sensitive adhesives are formulated using alkyl (alkyl)acrylate esters that are polymerized using non-aromatic initiator and cross-linkers. The concentration of unreacted components such a monomers, initiators, and crosslinkers should be minimized to insure low fluorescence. Typically, the concentration of unreacted monomers in the formulation will be in the ppm range When an organic solvent is used in the formulation, non-aromatic solvents such as low molecular weight hydrocarbons, alcohols, and esters are preferred. Solvents such as heptane, hexane, ethyl acetate and isopropanol are preferred. Reactive monomers such as acrylic acid may be inhibited using substituted hydroquinones. Substituted hydroquinones extend the shelf life of the reactive monomers and higher concentrations are used for the most reactive monomers. Substituted hydroquinones in the sealing layer may fluoresce significantly after exposure to radiant energy due to their low activation energy.

What is claimed is:

1. In a microfluidic in-vitro diagnostic device comprised of a base having at least one fluid channel within which a fluid sample to be assayed passes from an inlet port to a detection zone, the improvement comprising said at least one fluid channel being enclosed by at least one enclosure surface wherein at least one surface of the fluid channel comprises either a hydrophilic heat-sealable adhesive or a hydrophilic pressure sensitive adhesive, wherein the hydrophilic adhesive increases the surface energy of a fluid flow path through the channel and wherein the hydrophilic adhesive decreases the surface tension of a biological fluid flowing through the channel.

2. The microfluidic device of claim 1, wherein said enclosure surface is heat-sealed to said base to seal said at least one fluid channel by the hydrophilic heat-sealable adhesive.

3. The microfluidic device of claim 1, wherein the surface of said enclosure surface comprises a pressure sensitive adhesive.

4. The microfluidic device of claim 1, wherein said enclosure surface is comprised of a low fluorescent material.

5. The microfluidic device of claim 1, wherein said enclosure surface is comprised of a polymeric material with which a surfactant is admixed to provide hydrophilic surface properties.

6. The microfluidic device of claim 1, wherein said enclosure surface is comprised of a polymeric material having a surfactant applied to a surface thereof.

7. The microfluidic device of claim 5, wherein said surfactant is a non-ionic or anionic surfactant.

8. The microfluidic device of claim 7, wherein said surfactant is selected from the group consisting of polyethylene oxide, polypropylene oxide, nonylphenol ethoxylate and polyalkylene-oxide modified heptamethyltrisiloxane.

9. The microfluidic device of claim 7, wherein said surfactant is selected from the group consisting of sodium or ammonium salts of nonyl phenol ethoxyl sulfonic acid, sodium lauryl sulfate, sodium 2-ethylhexyl sulfate and sodium dioctylsulfo succinate.

10. The microfluidic device of claim 7, wherein said surfactant is selected from the group consisting of the ionic salt of 2-acrylamido-2-methyl propanesulfonic acid, N-vinyl caprolactam, caprolactone acrylate, N-vinyl pyrrolidone, and sulfate and acrylic monomers.

11. A biological detection device comprising:
a substrate providing a surface to carry a fluid from a first end of the substrate toward a detection zone along a fluid flow path, a portion of the substrate surface comprising a hydrophilic heat-sealable adhesive or a hydrophilic pressure sensitive adhesive wherein the hydrophilic adhesive increases the surface energy of the fluid flow path across the portion of the substrate surface comprising the hydrophilic adhesive and wherein the hydrophilic adhesive decreases the surface tension of a biological fluid flowing along the fluid flow path across the portion of the substrate surface comprising the hydrophilic adhesive.

12. The device of claim 11, wherein the hydrophilic adhesive comprises a polymeric material and at least one surfactant, wherein the surfactant increases the hydrophilicity of the polymeric material.

13. The device of claim 12, wherein the surfactant is selected from the group consisting of sodium salt of sulfated nonylphenol ethoxylate, ammonium salt of sulfated nonylphenol ethoxylate, sodium 2-ethyl hexyl sulfate, sodium octyl sulfate, sodium nonylphenol sulfate, nonyl phenol ethoxylate, sodium lauryl sulfate, sodium nonylphenol ether sulfate, polyalkylene oxide modified heptamethyl trisiloxane, sodium dioctyl sulfo succinate, and sodium salt of 2-acrylamide-2-methyl-propane sulfonic acid.

14. The microfluidic device of claim 5, wherein said surfactant is selected from the group consisting of sodium salt of sulfated nonylphenol ethoxylate, ammonium salt of sulfated nonylphenol ethoxylate, sodium 2-ethyl hexyl sulfate, sodium octyl sulfate, sodium nonylphenol sulfate, nonyl phenol ethoxylate, sodium lauryl sulfate, sodium nonylphenol ether sulfate, polyalkylene oxide modified heptamethyl trisiloxane, sodium dioctyl sulfo succinate, and sodium salt of 2-acrylamide-2-methyl-propane sulfonic acid.

15. The microfluidic device of claim 6, wherein said surfactant is selected from the group consisting of sodium salt of sulfated nonylphenol ethoxylate, ammonium salt of sulfated nonylphenol ethoxylate, sodium 2-ethyl hexyl sulfate, sodium octyl sulfate, sodium nonylphenol sulfate, nonyl phenol ethoxylate, sodium lauryl sulfate, sodium nonylphenol ether sulfate, polyalkylene oxide modified heptamethyl trisiloxane, sodium dioctyl sulfo succinate, and sodium salt of 2-acrylamide-2-methyl-propane sulfonic acid.

* * * * *